(12) United States Patent
Moroncini et al.

(10) Patent No.: US 9,150,634 B2
(45) Date of Patent: Oct. 6, 2015

(54) EPITOPES OF THE HUMAN PDGF RECEPTOR ABLE TO BIND HUMAN AUTO-ANTIBODIES, ANTIBODIES AND USES THEREOF

(76) Inventors: Gianluca Moroncini, Senigallia (IT); Ada Funaro, Turin (IT); Armando Gabrielli, Ancona (IT); Vittorio Enrico Avvedimento, Caserta (IT); Silvia Svegliati Baroni, Ancona (IT); Mariarosaria Santillo, Naples (IT); Roberto Paterno', Naples (IT)

( * ) Notice: Subject to any disclaimer, the term of this patent is extended or adjusted under 35 U.S.C. 154(b) by 0 days.

(21) Appl. No.: 13/812,764

(22) PCT Filed: Jul. 29, 2011

(86) PCT No.: PCT/EP2011/063165
§ 371 (c)(1),
(2), (4) Date: Jan. 28, 2013

(87) PCT Pub. No.: WO2012/013813
PCT Pub. Date: Feb. 2, 2012

(65) Prior Publication Data
US 2013/0130268 A1    May 23, 2013

Related U.S. Application Data

(60) Provisional application No. 61/369,292, filed on Jul. 30, 2010.

(51) Int. Cl.
| | | |
|---|---|---|
| C07K 7/00 | (2006.01) | |
| C07K 14/705 | (2006.01) | |
| C07K 14/71 | (2006.01) | |
| C07K 16/28 | (2006.01) | |
| C07K 5/10 | (2006.01) | |
| C07K 7/06 | (2006.01) | |
| C07K 7/08 | (2006.01) | |

(52) U.S. Cl.
CPC ............ *C07K 14/705* (2013.01); *C07K 5/10* (2013.01); *C07K 7/06* (2013.01); *C07K 7/08* (2013.01); *C07K 16/2863* (2013.01); *C07K 2317/34* (2013.01); *C07K 2317/515* (2013.01); *C07K 2317/52* (2013.01); *C07K 2317/565* (2013.01); *C07K 2317/75* (2013.01); *C07K 2317/92* (2013.01)

(58) Field of Classification Search
None
See application file for complete search history.

(56) References Cited

FOREIGN PATENT DOCUMENTS
WO    2007/013124 A2    2/2007

OTHER PUBLICATIONS

Nacci, Giulia: "Characterization and cloning of agonistic autoantibodies specific for the PDGF receptor from the B cell repertoire of SSc patients.", Thesis, Jan. 1, 2010,Retrieved from the Internet URL: http://dott-scsv.campusnet.unito.it/tesi/nacci_thesis.pdf.
Gabrielli, et al: "'Pathogenic autoantibodies in systemic sclerosis", Current Opinion in Immunology, Elsevier, Oxford, GB, vol. 19, No. 6, Dec. 14, 2007, pp. 640-645, ISSN: 0952-7915, DOI: 10.10161, J.COI.2007.11.004.
PCT Written Opinion of the International Preliminary Examining Authority mailed on Jul. 18, 2013 and PCT Notification Concerning Informal Commutations with the Applicant mailed on Oct. 24, 2012.
Kazuhiro Kurasawa, et al : "Autoantibodies against platelet-derived growth factor receptor alpha in patients with systemic lupus erythematosus", Modern Rheumatology , Official Journal of the Japan College of Rheumatology, Springer-Verlag, TO, vol. 20, No. 5, May 21, 2010, pp. 458-465; see paragraph Enzyme immunoassay for anti-PDGFR alpha antibody; see paragraph anti-POGFR alpha antibodies in the sera from patients with SLE.
Loizos, N., et al: "Lack of detection of agonist activity by antibodies to platelet-derived growth factor receptor [alpha] in a subset of normal and systemic sclerosis patient Sera", Arthritis and Rheumatism 2009 John Wiley and Sons Inc. USA, vol. 60 , No. 4, 2009 , pp. 1145-1151; RH column, first sentence of the first full paragraph.

*Primary Examiner* — Michael Pak
(74) *Attorney, Agent, or Firm* — Lucas & Mercanti, LLP

(57) ABSTRACT

The present invention refers to peptides comprised in the extracellular region of human PDGF receptor (hPDGFR) alpha, their use for detecting auto-antibodies anti-hPDGFR alpha and to a method for the diagnosis or the monitoring control for therapy of SSc. The present invention also refers to antibodies or recombinant or synthetic derivatives thereof able to recognize and bind to the above peptide and to their use in the treatment of SSc.

10 Claims, 24 Drawing Sheets a     PAM 13B8: 2 IgG ANTIBODIES

PAM 16F4: 2 IgG ANTIBODIES b

| | FR1 | CDR1 | FR2 | CDR2 |
|---|---|---|---|---|
| VH PAM | GLVKPLETLSLTCSVSGGSVSDG | SYEWN | WIRQPPGKGLEWIG | YAYSRGTNYNSPSLKG |
| | FR3 | | CDR3 | FR4 |
| | RITSVDKSKNQISLKLTSVTPADTAVYYCAR | | DSFEI | WGQGTMVTV |
| Vκ13B8 | FR1 | CDR1 | FR2 | CDR2 |
| | DIQMTQSPSSLSASVGDRVTITC | RASQGISNYLA | WFQQKPGKAPKSLIY | AASSLQS |
| | FR3 | | CDR3 | FR4 |
| | GVPSKFSGSGSGTDFTLTISSLQPEDFATYYC | | QQYNSFPYT | FGQGTKLEIK |
| Vλ13B8 | FR1 | CDR1 | FR2 | CDR2 |
| | QSVLTQPPSASGTPGQSITISC | SGSDSNIGNNYY | WYQQLSGMAPKLLIY | RNHQRPA |
| | FR3 | | CDR3 | FR4 |
| | GVPDRFSGSKSGTSASLAISGLRSEDEADYYC | | AAWEDGLSGPLWV | FGGGTKLTVL |
| Vκ16F4 | FR1 | CDR1 | FR2 | CDR2 |
| | DIQMTQSPDSLAVSLGERATINC | KSSQSVLYSSDNKNYLA | WYQQKPGQPPKLLIY | WASTRES |
| | FR3 | | CDR3 | FR4 |
| | GVPDRFSGSGSGTDFTLTISSLQAEDVAVYYC | | QQYYSTPKT | FGQGTKVEIK |
| Vλ16F4 | FR1 | CDR1 | FR2 | CDR2 |
| | QSALTQPASVSGSPGQSITISC | TGTSSDVGGYNYVS | WYQQHPGKAPKLMIY | EVSHRPS |
| | FR3 | | CDR3 | FR4 |
| | GVSNRFSGSKSGNTASLTISGLQAEDEADYYC | | SSYTSSSHVV | FGGGTKLTVL |

Fig. 3

ROM 1F5: 4 IgM ANTIBODIES

VκI3B8 + VH1 ROM a

IgM (pentamer)

VκI3B8 + VH2 ROM

IgM (pentamer)

b

VH1  
FR1: QVQLVQSGGGLVQPGGSLRLSCAASGFTFS  
CDR1: SYSMN  
FR2: WVRQAPGKGLEWVS  
CDR2: YISSSSSTIYYADSVKG  
FR3: RFTISRDNAKNSLYLQMNSLRAEDTAVYYCAR  
CDR3: VGYDFWSDYPYYYYMDV  
FR4: WGKGT

VH2  
FR1: QVQLQESGPGLVKPSQTLSLTCTVSGGSISSG  
CDR1: SYYWS  
FR2: WIRQPAGKGLEWIG  
CDR2: RIYTSGSTNYNPSLKS  
FR3: RVTISVDTSKNQFSLKLSSVTAADTAVYYCAR  
CDR3: DTPKTNLWNYVEWFDP  
FR4: WGQGT

Vκ13B8  
FR1: DIQMTQSPSSLSASVGDRVTITC  
CDR1: RASQGISNYLA  
FR2: WFQQKPGKAPKSLIY  
CDR2: AASSLQS  
FR3: GVPSKFSGSGSGTDFTLTISSLQPEDFATYYC  
CDR3: QQYNSFPLT  
FR4: FGQGT

Vλ1  
FR1: QSVLTQPPSVSGAPGQRVTISC  
CDR1: TGSSNVGAGYDVH  
FR2: WYQQLPGTAPKLLIY  
CDR2: GNSNRPS  
FR3: GVPDRFSGSKSGTSASLAITGLQAEDEADYYC  
CDR3: QSYDSSLALY  
FR4: FGGGT

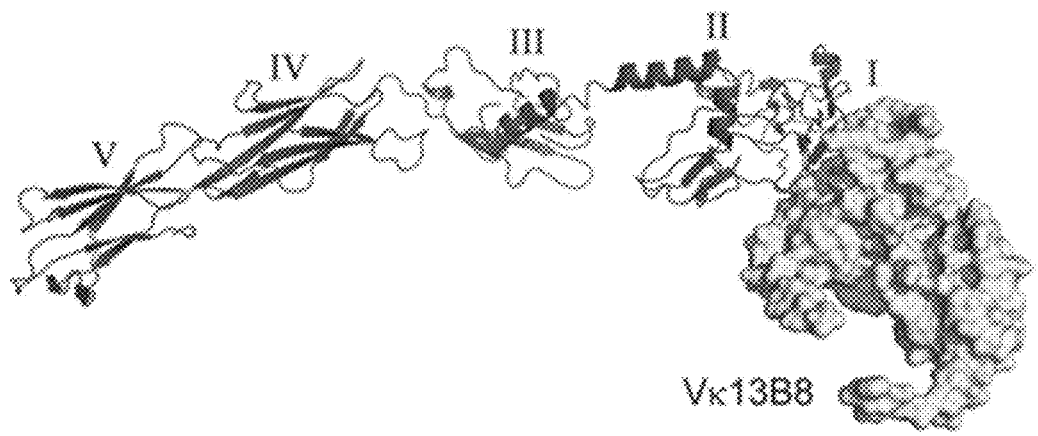

PDGFRα (1-304aa)

MGTSHPAFLVLGCLLTGLSLILCQLSLPSILPNENEKVVQLNSSFSLRCFG
ESEVSWQYPMSEEESSDVEIRNEENNSGLFVTVLEVSSASAAHTGLYTC
YYNHTQTEENELEGRHIYIYVPDPDVAFVPLGMTDYLVIVEDDDSAIIPCR
TTDPETPVTLHNSEGVVPASYDSRQGFNGTFTVGPYICEATVKGKKFQT
IPFNVYALKATSELDLEMEALKTVYKSGETIVVTCAVFNNEVVDLQWTYP
GEVKGKGITMLEEIKVPSIKLVYTLTVPEATVKDSGDYECAARQATREVK
EMKK...

MGTSHPAFLVLGCLLTGLSLLCQLSLPSILPNENEKVVQLNSSFSLRCFG
ESEVSWQYPMSEEESSDVEIRNEENNSGLFVTVLEVSSASAAHTGLYTC
YYNHTQTEENELEGRHIYIYVPDPDVAFVPLGMTDYLVIVSAIIPCR
TTDPETPVTLHNSEGVVPASYDSRQGFNGVGPYICEATVKGKKFQT
IPFNVYALKATSELDLEMEALKTVYKSGETIVVTCAVFNNEVVDLQWTYP
GEVKGKGITMLEEIKVPSIKLVYTLTVPEATVKDSGDYECAAR
MKK...

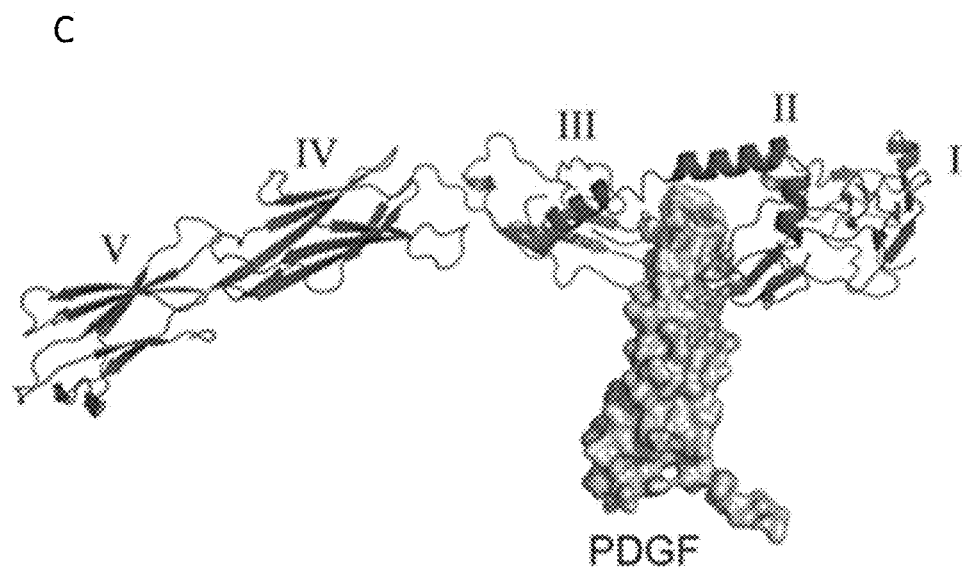

MGTSHPAFLVLGCLLTGLSLILCQLSLPSILPNENEKVVQLNSSFSLRCFG
ESEVSWQYPMSEEESSDVEIRNEENNSGLFVTVLEVSSASAAHTGLYTC
YYNHTQTEENELEGRHIYIYVPDPDVAFVPLGMTDYLVIVEDDDSAIIPCR
TTDPETPVTLHNSEGVVPASYDSRQGFNGTFTVGPYICEATVKGKFQT
IPFNVYALKATSELDLEMEALKTVYKSGETIVVTCAVFNNEVVDLQWTYP
GEVKGKGITMLEEIKVPSIKLVYTLTVPEATVKDSGDYECAARQATTREVK
EMKK...

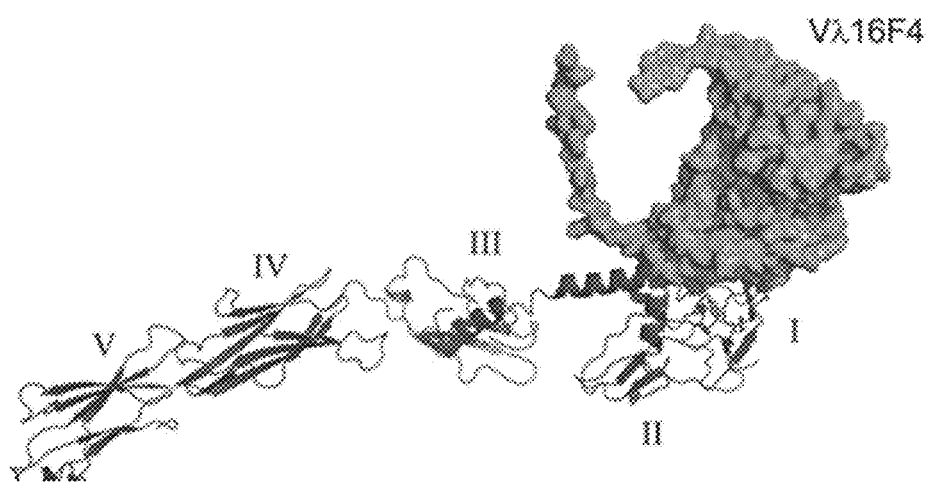

MGTSHPAFLVLGCLLTGLSLILCQLSLPSILPNENEKVVQL░░░░SLRCFG
ESEVSWQYPMSEEESSDVEIRNEENNSGLFV░░░░░░░░TGLYTC
YYNHTQTEENELEGRHIYIYVPDPDVAFVPLGMTDYLVIVEDDDSAIIPCR
TTDPETPVTLHNSEGVVPASYDSRQGFNGTFTVGPYICEATVKGKKF░░
░░░░YALKATSELDLEMEALKTVYKSGETIVVTCAVFNNEVVDLQWTYP
GEVKGKGITMLEEIKVPSIKLVYTLTVPEATVKDSGDYECAARQATREVK
EMKK...

Fig. 7

EPITOPES OF THE HUMAN PDGF RECEPTOR ABLE TO BIND HUMAN AUTO-ANTIBODIES, ANTIBODIES AND USES THEREOF

CROSS-REFERENCE TO RELATED APPLICATIONS

This application is a 371 of PCT/EP2011/063165, filed Jul. 29, 2011, which claims the benefit of U.S. Provisional Application No. 61/369,292, filed Jul. 30, 2010, the contents of each of which are incorporated herein by reference.

FIELD OF THE INVENTION

The present invention refers to peptides comprised in the extracellular region of human PDGF receptor (hPDGFR) alpha, their use for detecting auto-antibodies anti-hPDGFR alpha and to a method for the diagnosis or the monitoring control for therapy of SSc. The present invention also refers to antibodies or recombinant or synthetic derivatives thereof able to recognize and bind to the above peptide and to their use in the treatment of SSc, to nucleic acids molecule encoding for the above antibody or recombinant or synthetic derivative and their use for the diagnosis or the monitoring control for therapy of SSc.

BACKGROUND OF THE INVENTION

Scleroderma (Systemic Sclerosis; SSc) is a relatively rare and often fatal disorder that affects mostly adult women. SSc is characterized by microvasculature damage, inflammation and autoimmunity, and fibroblasts activation leading to massive fibrosis in the connective tissue of skin, vessels, muscles and visceral organs. Organ involvement, disease progression and clinical severity vary greatly amongst affected individuals, with death occurring as the result of end-stage organ failure. In spite of significant effort, SSc pathogenesis remains ill-defined and consequently, disease outcome is often unpredictable and clinical treatment is very limited. Authors have discovered in the serum of patients affected by some autoimmune diseases, a new type of autoantibodies, targeting the human PDGF receptor (PDGFR) (WO2007/013124). Serum anti-PDGFR auto-antibodies may represent a main determinant of the pro-fibrotic phenotype of scleroderma fibroblasts, since they can convert healthy human fibroblasts into SSc-like cells characterized by excessive reactive oxygen species (ROS) production, stabilization of Ha-Ras, and amplified transcription of collagen genes (Baroni S S et al. N Engl J Med 2006; 354: 2667-2676).

PDGFR alpha and beta each contains five extracellular immunoglobulin-like domains and an intracellular tyrosine kinase domain. Ligand binding to the extracellular domains induces receptor dimerization and tyrosine phosphorylation, activating several downstream signaling pathways (Heldin C H, Biochimica et Biophysica Acta 1998), some of which are directly or indirectly linked to extracellular matrix regulation. Recently, a study by Olson and Soriano (Olson L E, Soriano P. Dev Cell 2009; 16: 303-313) has confirmed the central role of increased PDGFR activation and signaling in driving systemic fibrosis in vivo in transgenic mice.

SUMMARY OF THE INVENTION

Specific and unequivocal detection of anti-PDGFR auto-antibodies in the serum of patients affected by SSc was shown to be problematic. This was mainly due to lack of robust cellular readout systems and technical limitations caused by the need to use high concentrations of total class G immunoglobulins (IgG) purified from serum samples of SSc patients and control subjects. These drawbacks led to conflicting reports (Classen J F et al. Arthritis & Rheum 2009; 60(4): 1137-1144; Loizos N et al. Arthritis & Rheum 2009; 60(4): 1145-1151; comments in: Dragun D et al. Arthritis & Rheum 2009; 60(4): 907-911; Gabrielli A et al. Arthritis Rheum. 2009; 60(11):3521-2) that questioned the existence of the agonistic autoimmune reaction to PDGFR as a potential pathogenic mechanism of SSc. To address this controversial issue, authors investigated the presence of PDGFR auto-reactive memory B cells in peripheral blood of SSc patients. This study not only confirmed the existence of an autoimmune process targeting the endogenous PDGFR in SSc patients, but also resulted into a dissection of the PDGFR-specific autoimmune repertoire of SSc patients providing new improved diagnostic and therapeutic tools. Authors exploited anti-PDGFR immunoglobulin genes isolated from the repertoire of SSc patients to generate agonistic and non-agonistic recombinant human monoclonal auto-antibodies (rHu-maab) directed to PDGFR. These novel reagents were employed to define the map of PDGFR functional domains involved in SSc-specific pathogenic intracellular signaling and PDGFR epitopes apparently unrelated to signaling pathways. These unprecedented observations open new perspectives to understand the pathogenesis of SSc and to devise novel diagnostic and therapeutic strategies against this complex disorder of the connective tissue. Moreover, the functional characterization of the extracellular domains of PDGFR, an ubiquitous receptor involved in several biological processes, may also have important implications in other contexts relevant to both physiological and pathological conditions.

Therefore, it is an object of the present invention a peptide having an amino acid sequence comprised in the extracellular region of human PDGF receptor (hPDGFR) alpha said region consisting of aa. 1-304 of SEQ ID NO. 1 (hPDGFR alpha; UniProtKB accession No. P16234) wherein said peptide is an epitope for auto-antibodies anti-hPDGFR alpha.

In an embodiment of the invention, said peptide comprises aa. 172-186, and/or aa. 141-152 and/or 294-301 of SEQ ID No. 1, preferably it essentially consists of aa. 172-186, and/or aa. 141-152, and/or 294-301 of SEQ ID No. 1 or of aa. 167-190, and/or aa. 138-154, and/or 290-306 of SEQ ID No. 1.

In another embodiment of the invention, said peptide comprises aa. 36-50 of SEQ ID No. 1, preferably it essentially consists of aa. 36-50 of SEQ ID No. 1.

In another embodiment of the invention, said peptide of the invention comprises aa. 42-45 and/or aa. 83-94 and/or aa. 199-205 of SEQ ID No. 1, preferably it essentially consists of aa. 42-45 and/or aa. 83-94 and/or aa. 199-205 of SEQ ID No. 1.

Another object of the invention is the use of at least one peptide of the invention for detecting auto-antibodies anti-hPDGFR alpha in a biological fluid isolated from a subject, preferably said subject being suspected to be a SSc affected subject.

A further object of the invention is a method for the diagnosis or the monitoring control for therapy of SSc characterized in detecting auto-antibodies anti-hPDGFR alpha in a biological fluid isolated from a subject by means of binding to at least one peptide of the invention.

Another object of the invention is an antibody or a recombinant or synthetic derivative thereof able to recognize and bind to at least one peptide of the invention, wherein the VH chain preferably comprises a CDR 3 region consisting of the aa. 91-95 of SEQ ID No. 3 (VHPAM as defined in FIG. 3).

More preferably, the VH chain of the above antibody or recombinant or synthetic derivative thereof further comprises a CDR 2 region consisting of the aa 43-58 of SEQ ID No. 3 and/or a CDR 1 region consisting of the aa. 24-28 of SEQ ID No. 3.

Even more preferably, the VH chain of the above antibody or recombinant or synthetic derivative thereof comprises essentially the sequence of SEQ ID No. 3.

The VL chain of the antibody or recombinant or synthetic derivative thereof of the invention preferably comprises a CDR 3 region consisting of one of the aa sequences belonging to the following group: the aa. 95-103 of SEQ ID No. 6 (Vk16F4 as defined in FIG. 3); the aa. 89-97 of SEQ ID No. 4 (Vk13B8 as defined in FIG. 3); the aa. 91-100 of SEQ ID No. 7 (Vlambda16F4 as defined in FIG. 3), more preferably it further comprises a CDR 2 region consisting of one of the aa sequences belonging to the following group: the aa. 56-62 of SEQ ID No. 6; the aa. 50-56 of SEQ ID No. 4; the aa. 52-58 of SEQ ID No. 7 and/or a CDR 1 region consisting of one of the aa sequences belonging to the following group: the aa. 24-40 of SEQ ID No. 6; the aa. 24-34 of SEQ ID No. 4; the aa. 23-36 of SEQ ID No. 7.

Even more preferably, the VL chain of the above antibody or recombinant or synthetic derivative thereof comprises essentially the aa. sequence of SEQ ID No. 6; the aa. sequence of SEQ ID No. 4; or the aa. sequence of SEQ ID No. 7.

The antibody or a recombinant or synthetic derivative thereof of the invention preferably essentially consists of the aa. sequence of SEQ ID No. 12 (rHumaab VK16F4 having the following sequence:

QVQLQESGPGLVKPLETLSLTCSVSGGSVSDG<u>SYFWN</u>WIRQPPGKGLEWIG<u>YAYSRGTTNYSPS</u>

LKGRITISVDKSKNQISLKLTSVTPADTAVYYCAR<u>DSFEI</u>WGQGTMVTVASASTKGPSV

DIQMIQSPDSLAVSLGERATINC<u>KSSQSVLYSSDNKNYLA</u>WYQQKPGQPPKLLLY<u>WASTRESGV</u>

PDRFSGSGSGTDFTLTISSLQAEDVAVYYC<u>QQYYSTPKT</u>FGQGTKVEIKRTVAAPSVF wherein CDR3 are underlined).

In another embodiment the antibody consists of a VH chain essentially consisting of the aa. sequence of SEQ ID No. 8 (VH1 as defined in FIG. 4) or 9 (VH2 as defined FIG. 4) and of a VL chain essentially consisting of the aa. sequence of SEQ ID No. 10 (Vk13B8 as defined in FIG. 4) or 11 (Vlambda1 as defined in FIG. 4).

A further object of the invention is the antibody or a recombinant or synthetic derivative thereof of the invention being an agonist of hPDGFR.

Objects of the invention are the antibody or a recombinant or synthetic derivative thereof according to the invention for medical use, preferably for medical use in the treatment of SSc, and a method of treatment of SSc consisting in administering a therapeutically effective amount of the antibody or a recombinant or synthetic derivative thereof of the invention to a SSc affected subject.

Other objects of the invention are a nucleic acid molecule encoding for any of the antibodies or recombinant or synthetic derivatives thereof of the invention, its use for the diagnosis or the monitoring control for therapy of SSc and a method for the diagnosis or the monitoring control for therapy of SSc characterized in detecting said nucleic acid in a cell sample isolated from a subject.

BRIEF DESCRIPTION OF THE DRAWINGS

The present invention will be described through non-limitative examples, with reference to the following figures.

DETAILED DESCRIPTION OF THE INVENTION

Figure 1:
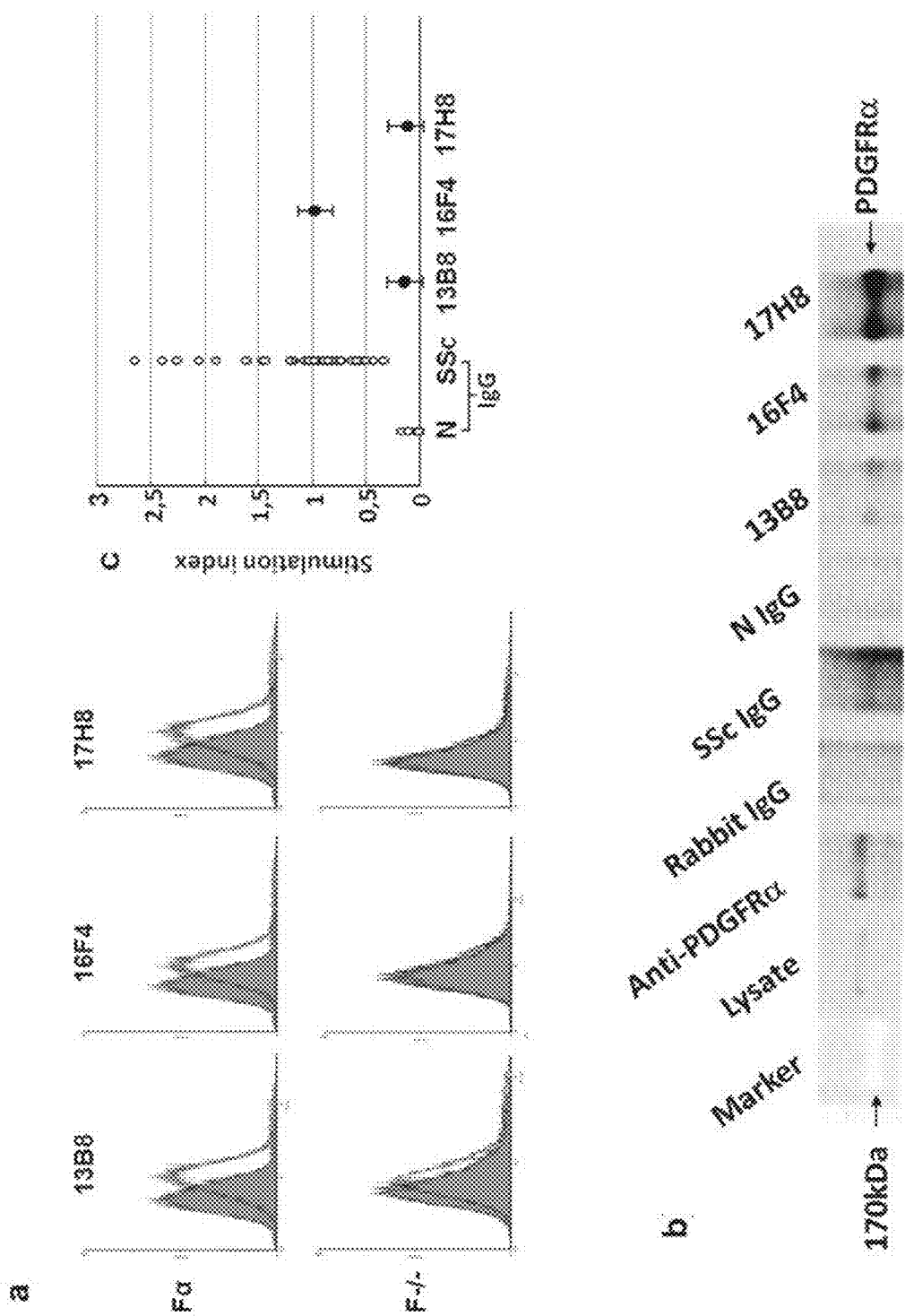
FIG. 1 Memory B cells isolated from PBMC of SSc patients produce IgG that bind to and stimulate PDGFR alpha. PAM is the patient code. IgG were purified from serum-free supernatants of the memory B cell lines PAM 13B8, 16F4, 17H8 and used (10 micrograms/ml) in three independent assays. (a) Cytofluorimetric analysis of the reactivity of IgG produced by PAM 13B8, 16F4, 17H8 cell lines on mouse fibroblasts derived from PDGFR-knockout embryos, transfected with the full-length human PDGFR alpha (F alpha) cells (top panels, white profile). No reactivity was observed in PDGFR alpha knock out vector-transfected mouse fibroblasts (F−/−) (bottom panels), indicating specificity of the staining. The shaded profile is the isotype-matched negative control. (b) Immunoprecipitation and Western blot analysis of PDGFR alpha from normal human fibroblasts total cell extracts. Rabbit polyclonal anti-PDGFR alpha antibody and rabbit IgG (10 micrograms/ml) were used as positive and negative control, respectively. Additional immunoprecipitating reagents were total IgG (200 micrograms/ml) purified from serum of SSc patients (SScIgG) and healthy controls (NIgG). Immunoprecipitated PDGFR alpha was visualized by immunoblotting with a rabbit anti-PDGFR alpha antibody-HRP. (c) Reactive Oxygen Species (ROS) assay. Only IgG produced by PAM 16F4 cell line induced ROS production in F alpha cells. ROS levels elicited by PAM 16F4 IgG were comparable to the average levels induced by total IgG purified from serum of SSc patients. Conversely, IgG produced by PAM 13B8 and 17H8 cell lines did not stimulate ROS production, like total IgG purified from serum of healthy controls (N).
Figure 2:
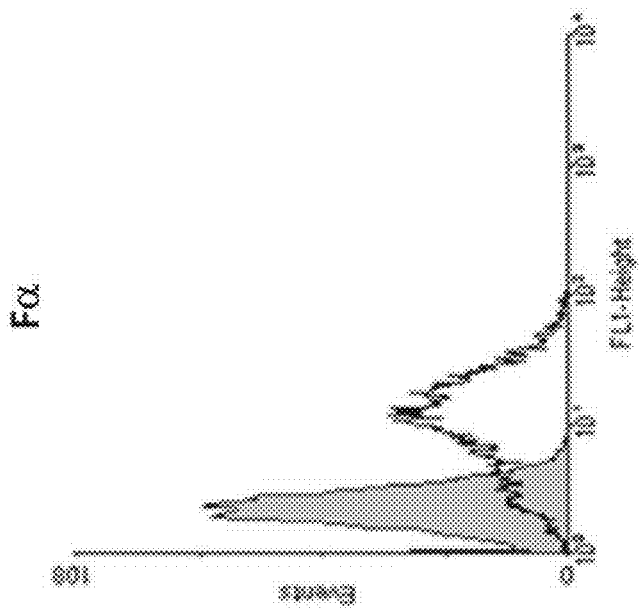
FIG. 2 Memory B cells isolated from PBMC of SSc patients produce IgM that bind to and stimulate PDGFR alpha. ROM is the patient code. Serum-free supernatant of the memory B cell line ROM 1F5 was used in two independent assays. (a) Cytofluorimetric analysis of the reactivity of IgM produced by ROM 1F5 cell line on F alpha cells (white profile). No reactivity was observed in PDGFR alpha knock out F−/− cells, indicating specificity of the staining. The shaded profile is the isotype-matched negative control. (b) ROS assay. IgM produced by ROM 1F5 cell line induced ROS production in F alpha cells. ROS levels elicited by ROM 1F5 IgM were comparable to the average levels induced by total IgG purified from serum of SSc patients.
Figure 2:
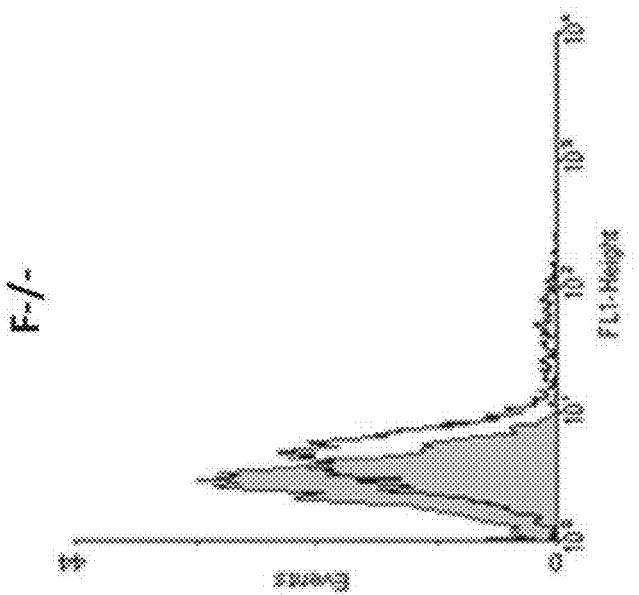
Figure 2:
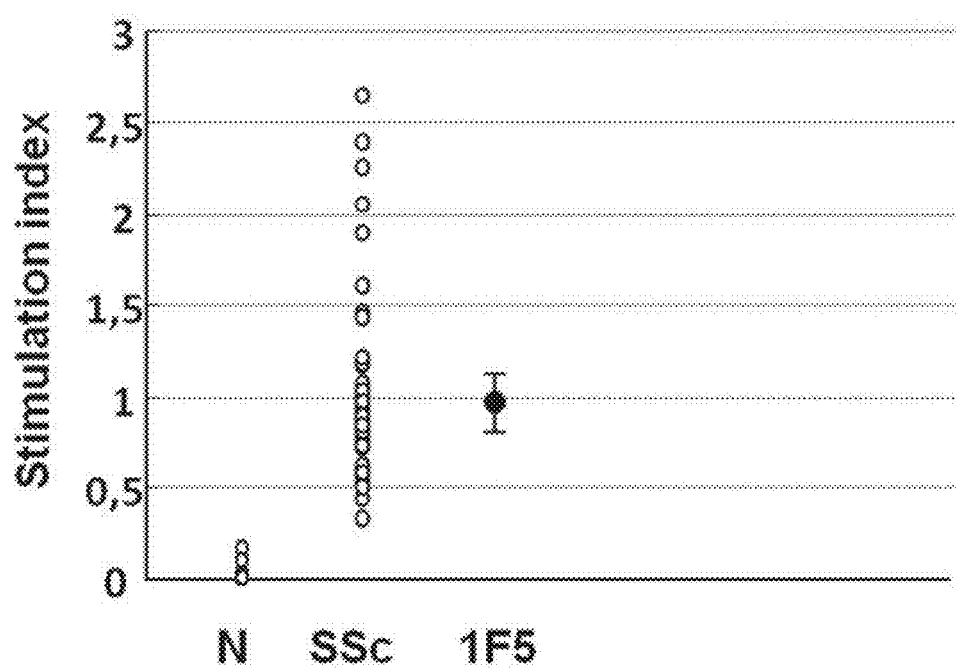
Figure 3:
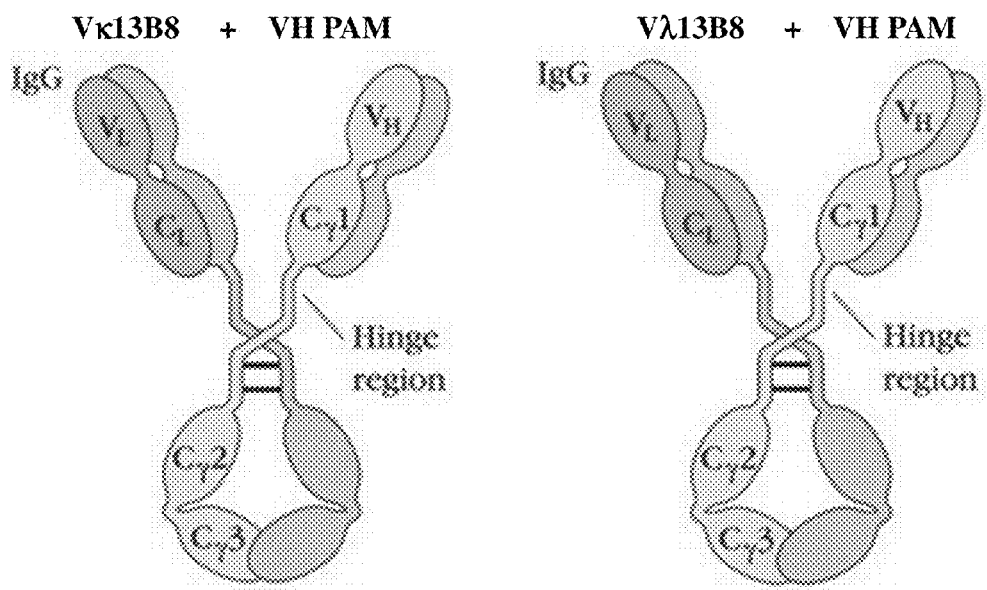
FIG. 3 Immunoglobulin repertoire of PDGFR auto-reactive B cells isolated from one scleroderma patient (PAM). (a) Restricted repertoire of PDGFR autoreactive B cells. Schematic of VH and VL chains pairings found in PAM 13B8 and 16F4 IgG positive, memory B cell lines. The repertoire of PAM 17H8 was identical to 13B8, therefore it was not reported in the figure. The same pairings indicated here were subsequently used to generate the 4 novel rHumaab, denoted by the 4 different VL chains. (b) Sequence of PCR amplified immunoglobulin cDNA fragments derived from each oligoclonal B cell line. A restricted panel composed of one VH and four VL sequences was found. The unique VH sequence, shared by all of the three B cell lines, was designated as VH PAM. The VL sequences were denoted according to the k or lambda subgroups and to the numbering of PAM B cell culture in which they were first identified. (c) Melting curves obtained by real-time PCR performed with VH PAM CDR3-specific primers. SSc and healthy control samples are shown in the upper and lower panel, respectively. In both panels, the highest fluorescence peak corresponds to the specific melting temperature (84° C.) obtained upon amplification of PAM cDNA (SSc positive control). The same melting curve was identified in SSc patients' cDNA (n=20). Fluorescence intensity of such peak was higher in cDNA of SSc patients compared to healthy subjects (n=20), that are characterized by a less pronounced specific melting product and additional, non-specific products.
Figure 3:
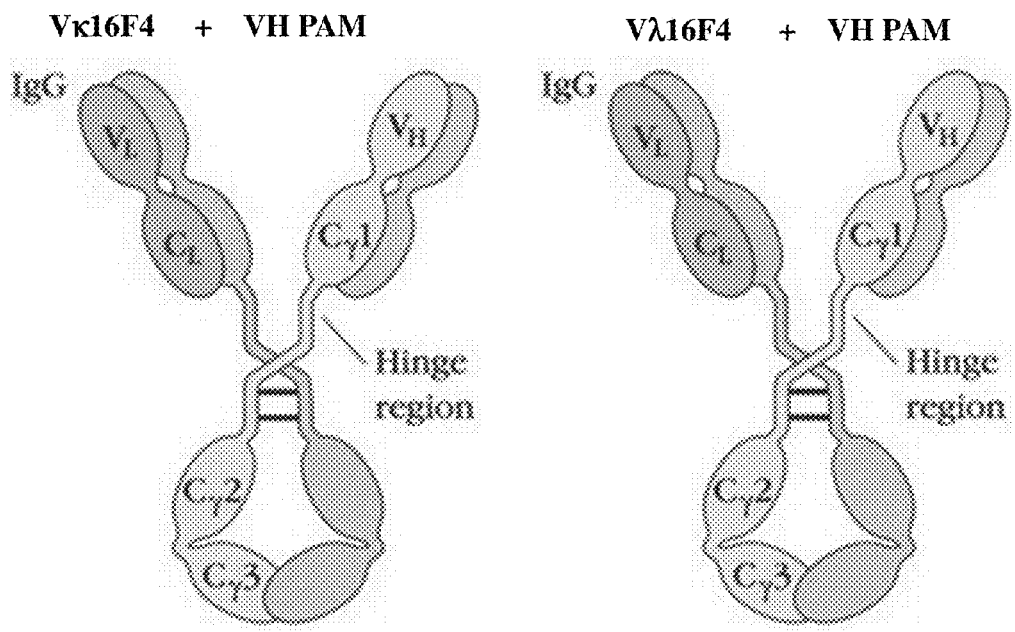
Figure 3:
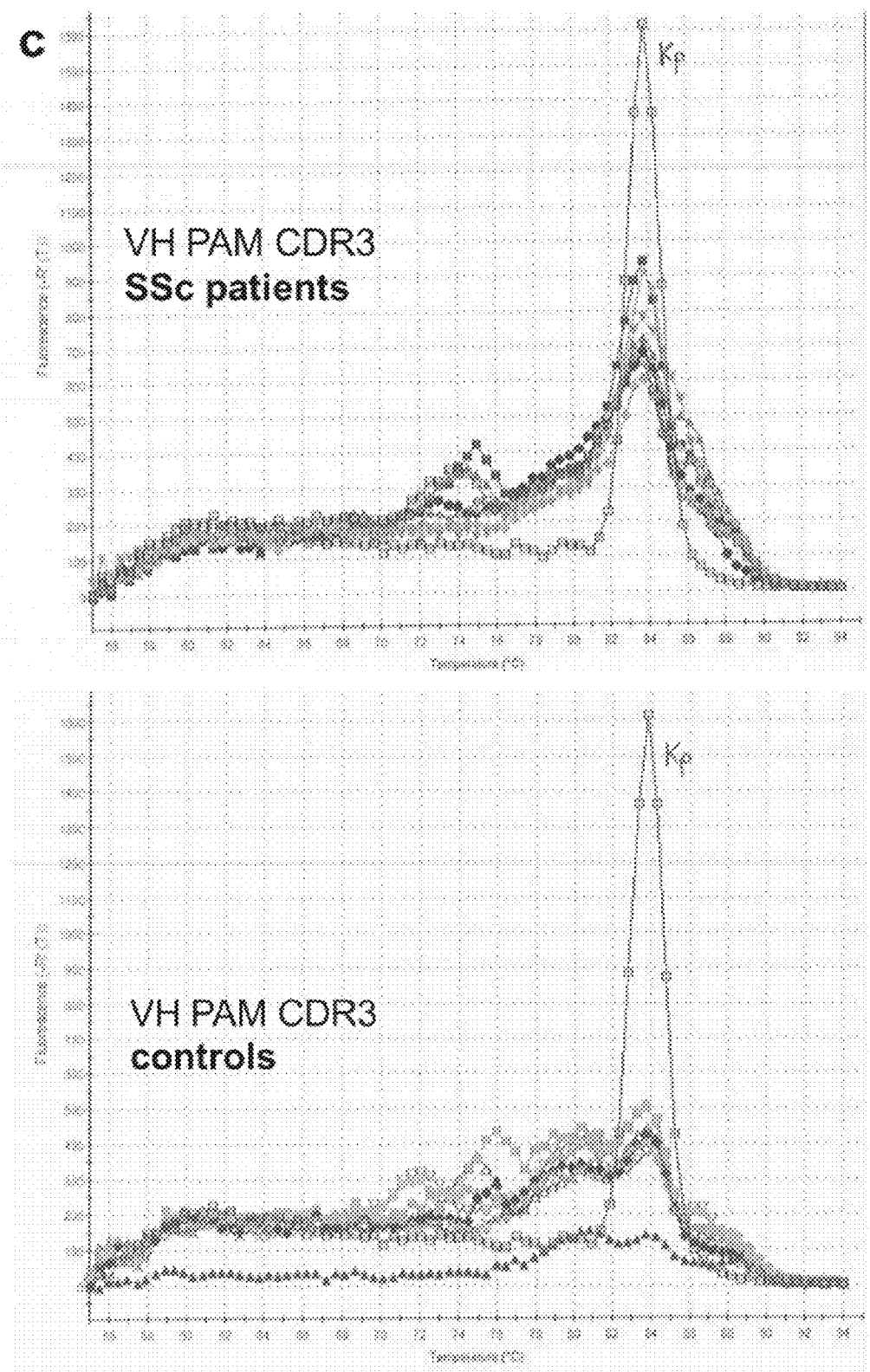
Figure 4:
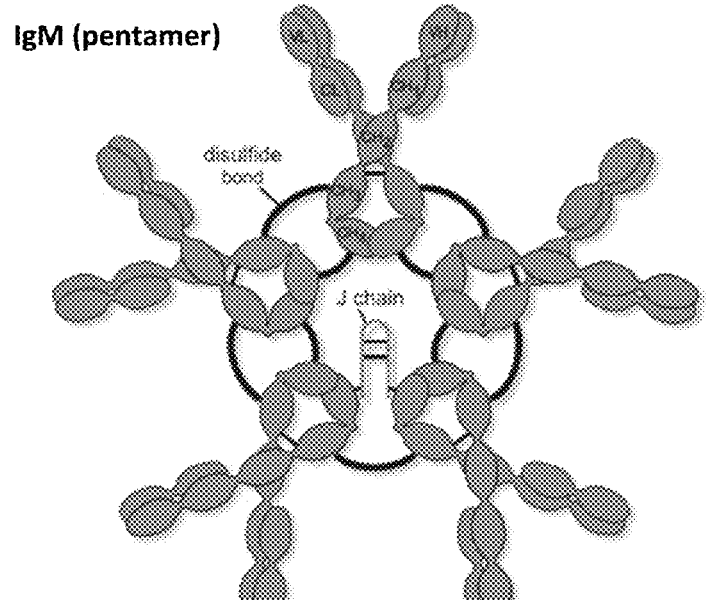
FIG. 4 Immunoglobulin repertoire of PDGFR auto-reactive B cells isolated from one scleroderma patient (ROM). (a) Restricted repertoire of PDGFR autoreactive B cells. Schematic of VH and VL chains pairings found in ROM1F5 IgM positive, memory B cell line. The same pairings indicated here were subsequently used to generate 4 novel rHumaab. (b) Sequence of PCR amplified immunoglobulin cDNA fragments derived from ROM1F5 oligoclonal B cell line. A restricted panel composed of two VH and two VL sequences was found. The two VH sequences were designated as VH1 and VH2. The VL sequences were denoted according to the k or lambda subgroups; the Vk was designated according to the numbering of PAM B cell culture in which it was first identified (Vk 13B8).
Figure 4:
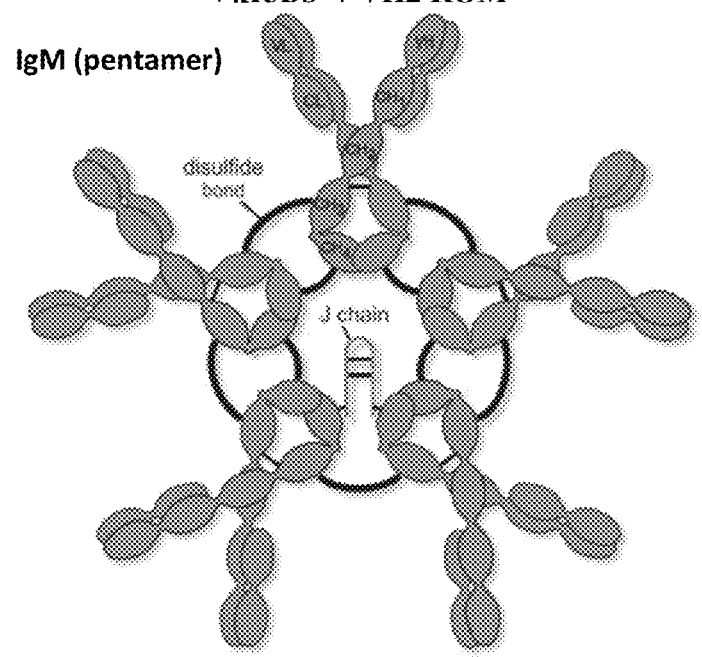
Figure 4:
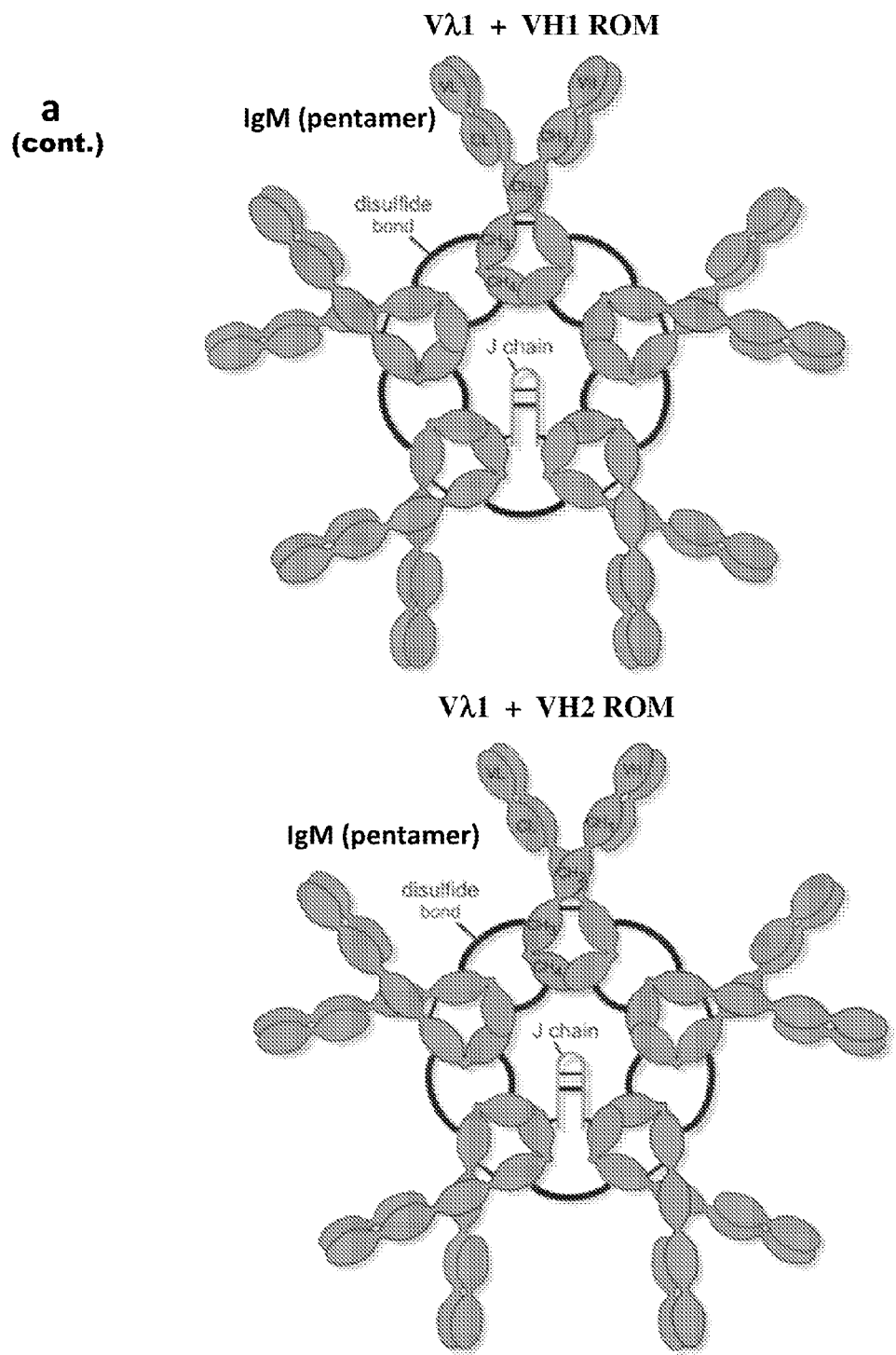

Results
Immunoglobulin Repertoire of PDGFR Auto-Reactive Oligoclonal B Cells Isolated from Blood of SSc Patients
Memory B cells were isolated from the peripheral B cell repertoire of patients affected by systemic sclerosis (SSc) and immortalized by EBV, as described previously (Funaro A, et al. BMC Biotechnology 2008; 8: 85). Reactivity of these B cell culture supernatants to PDGFR alpha was demonstrated by immunofluorescence and flow cytometry analysis, using mouse fibroblasts derived from PDGFR-knockout embryos, transfected with full-length human PDGFR alpha (F alpha) as target cells. Cell culture supernatants showing reactivity with F alpha cells were counter-selected on mock-transfected mouse fibroblasts (F−/−). Three B cell lines (namely, PAM 13B8, PAM 16F4 and PAM 17H8) characterized by production of IgG selectively binding to F alpha, but not to F−/− cells, were identified in one patient (coded as PAM) and expanded in serum-free medium (FIG. 1a). IgG were purified from B cell supernatants and used to immunoprecipitate PDGFR alpha from human fibroblast extracts and to induce production of reactive oxygen species (ROS) in human fibroblasts. All of these three B cell lines produced IgG able to bind to native human PDGFR alpha (FIG. 1b), but only one (PAM 16F4) showed agonistic activity, documented by its ability to elicit ROS production (FIG. 1c). The same methodology was applied to peripheral blood of a second patient (coded as ROM). In this case, one B cell line (ROM 1F5) characterized by production of IgM selectively binding to F alpha, but not to F−/− cells, and inducing ROS production in human fibroblasts, was identified (FIG. 2a-b). To characterize in detail the selected IgG and IgM, RNA was extracted from each B cell line, reverse-transcribed into cDNA and sequenced with a set of primers aptly designed to analyze the entire human Ig gene repertoire. A restricted panel of variable (V) heavy (H) and light (L) chain IgG and IgM sequences was found in each B cell line. The repertoire of PAM 13B8 and 17H8 cell lines was nearly identical and was constituted by two VL chain sequences (one Vk and one Vlambda), whereas the repertoire of PAM 16F4 cell line included two independent VL chain sequences (one Vk and one Vlambda) and one Vlambda sequence shared with PAM 13B8 and 17H8. One common VH chain sequence (indicated as VH PAM) was found in all of the three oligoclonal B cell lines (FIG. 3a-b). ROM repertoire was characterized by two independent VH chain sequences, and two VL chain sequences. Of these, the Vk sequence was identical to that found in PAM 13B8 and 17H8, whereas the Vlambda sequence was original (FIG. 4a-b). Alignment of these sequences with the existing Ig data banks showed that the complementarity determining regions 3 (CDR3) are unprecedented. To verify that these CDR3 are a hallmark of SSc patients' immunoglobulin repertoire, we investigated the presence of VH PAM CDR3 transcripts in the mRNA of SSc patients (n=20) and healthy subjects (n=20) by PCR. Qualitative analysis (i.e. the melting curves of the amplified cDNA) showed a remarkable homogeneity of the amplified products derived from RNA of SSc patients compared to those derived from RNA of healthy subjects (FIG. 3c).

Anti-PDGFR Human Monoclonal Antibody Engineering and Characterization

Figure 5:
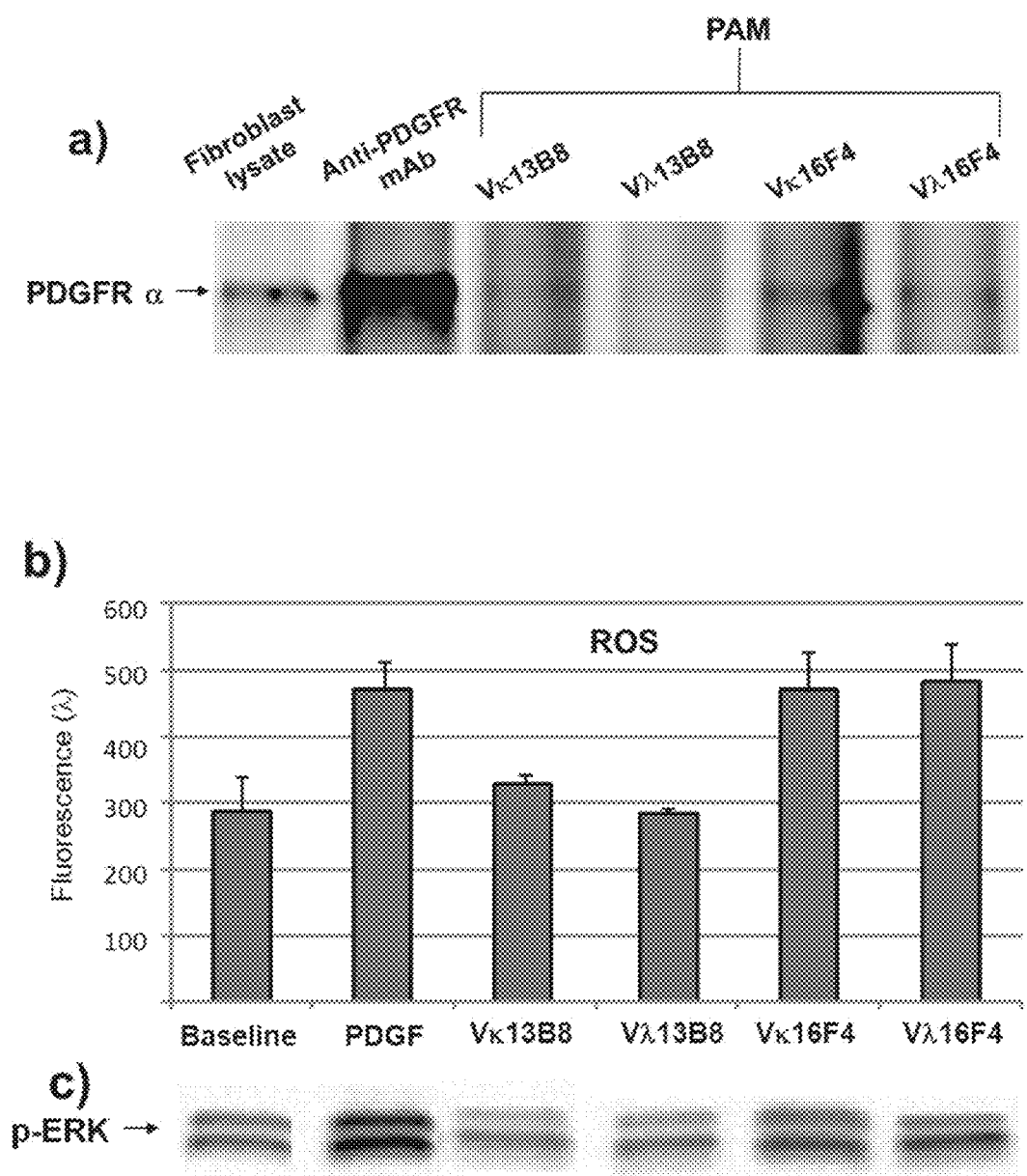
FIG. 5 Characterization of recombinant human monoclonal auto-antibodies (rHumaab). IgG were affinity-purified from serum-free supernatants of CHO cells stably transfected with each of the four rHumaab constructs and used (10 micrograms/ml) in four independent assays. Each result is representative of three experiments performed under the same conditions. (a) Vk13B8, Vk16F4 and Vlambda16F4, but not Vlambda13B8 rHumaab, immunoprecipitated PDGFR alpha from normal human fibroblast extracts. A mouse monoclonal anti-PDGFR alpha antibody was used as positive control. Immunoprecipitated PDGFR alpha was visualized by immunoblotting with rabbit anti-PDGFR alpha antibody-HRP. (b-c) Vk16F4 and Vlambda16F4, but not Vk13B8 and Vlambda13B8 rHumaab, induced (b) ROS production and (c) increased ERK phosphorylation (p-ERK) in normal human fibroblasts after 15 minutes incubation. Levels of ROS and p-ERK in fibroblasts at baseline and upon 15 minutes incubation with PDGF-BB are shown. Intracellular ROS production was measured by DCFH-DA fluorescence. Total proteins extracted from fibroblasts at baseline and after stimulation with the indicated reagents were immunoblotted with a mouse monoclonal antibody specific for p-ERK. (d) Vk16F4, but not the other rHumaab, induced increase of type I collagen gene transcription in normal human fibroblasts after 1 hour incubation. Type I A1 and A2 collagen gene expression was measured by quantitative real-time PCR in RNA extracted from fibroblasts at baseline and after stimulation with the indicated reagents. 24 hours stimulation with TGF beta was used as positive control, 1 hour PBS was used as antibody vehicle control. (e) Time course of collagen gene transcription in normal human fibroblasts challenged with Vk16F4 rHumaab or PDGF-BB. Vk16F4 induced stable increase of type I collagen gene transcription in normal human fibroblasts up to 24 hours incubation, with a peak at 6 hours. PDGF-BB did not display such a prolonged stimulatory activity on collagen gene transcription, since its effect was lost after 6 hours. 24 hours stimulation with TGF beta was used as positive control. (f) Vk16F4-induced collagen gene increase in fibroblasts is dependent on the presence of PDGFR alpha. Mouse fibroblasts derived from PDGFR-knockout embryos, transfected with full-length human PDGFR alpha (F alpha) or mock (F−/−) were used. Mouse collagen gene expression was measured by quantitative real-time PCR in RNA extracted from F alpha and F−/− fibroblasts at baseline and after 1 hour stimulation with Vk16F4 rHumaab or human PDGF-BB.
Figure 5:
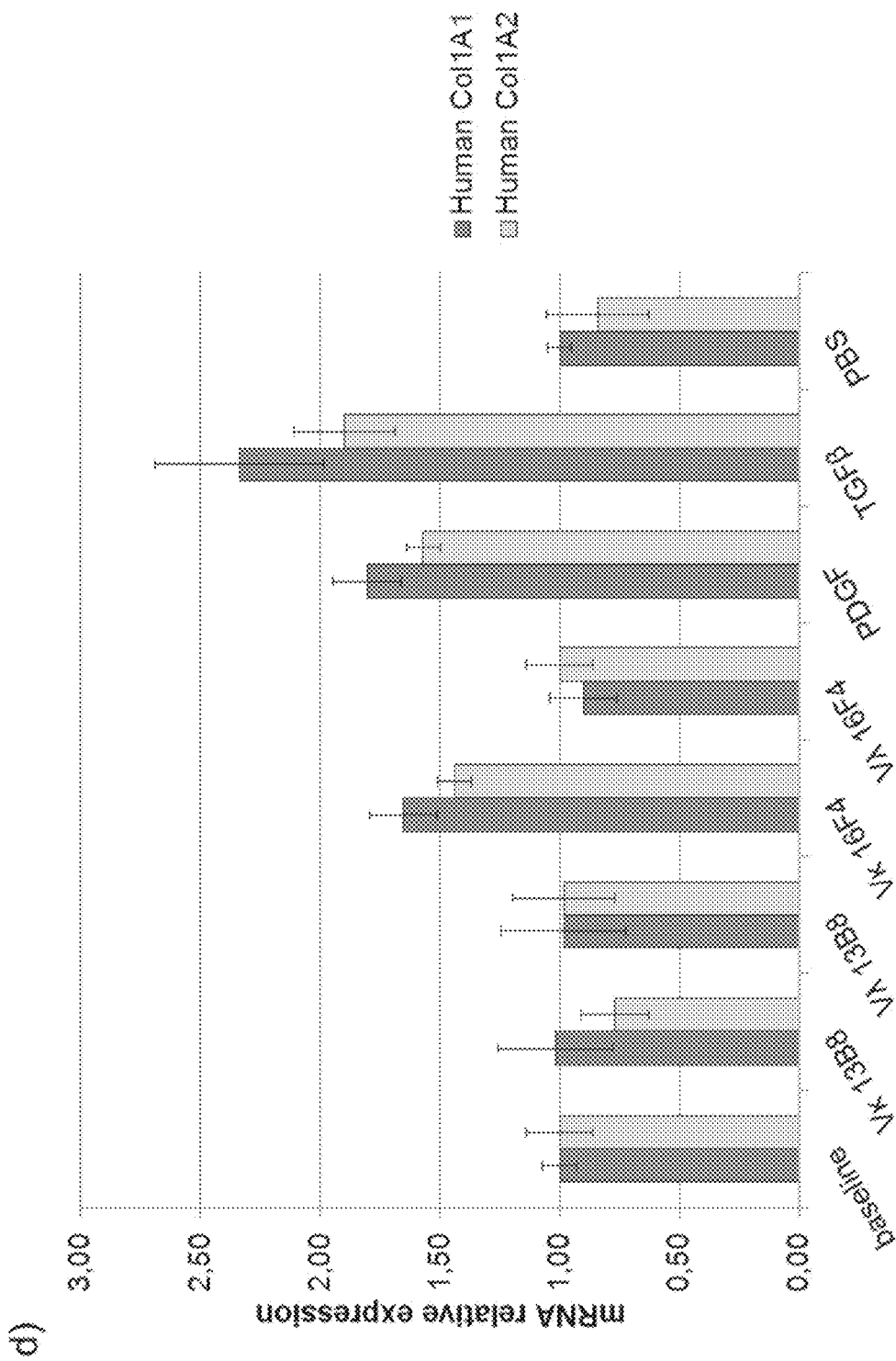
Figure 5:
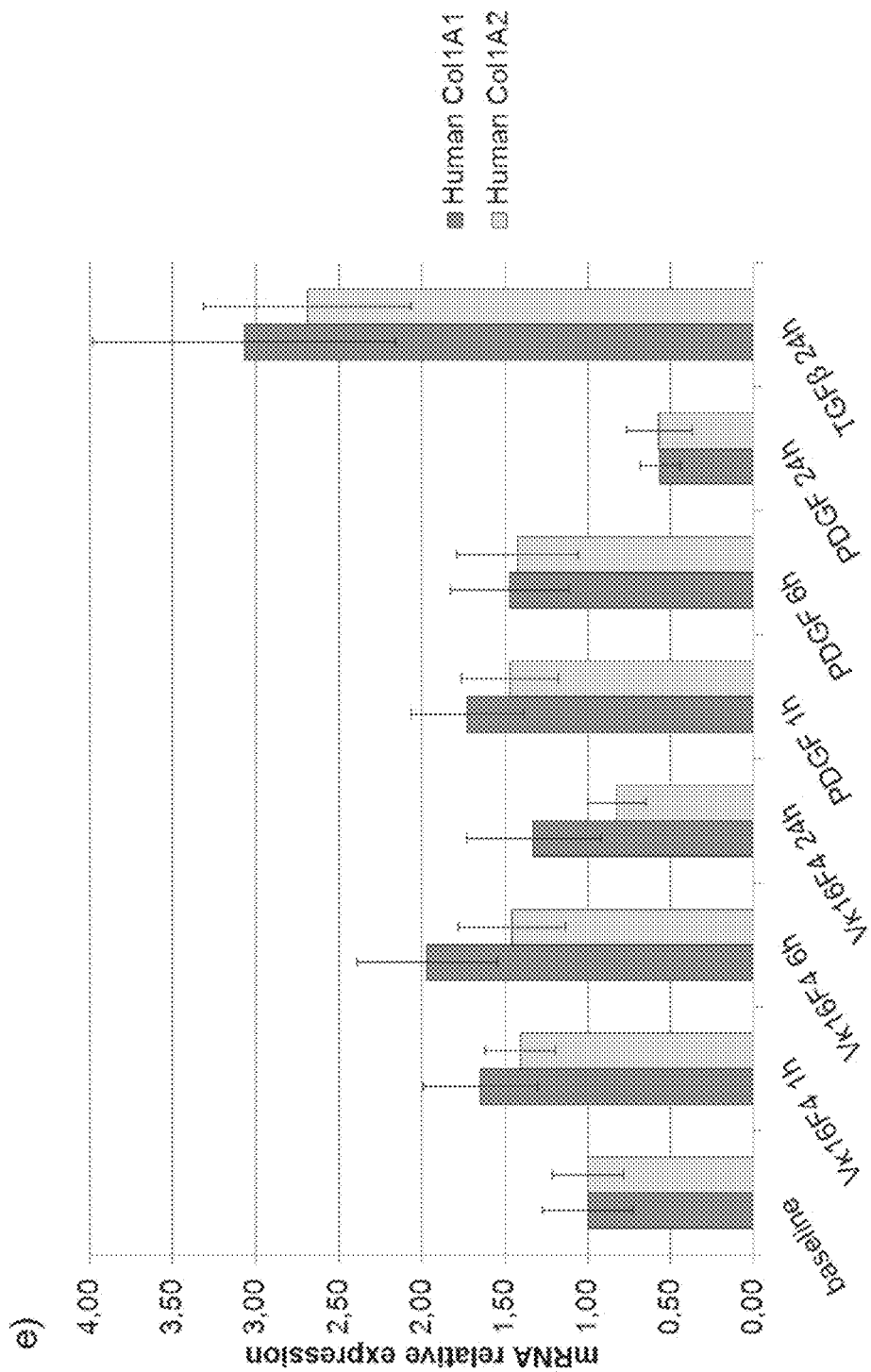
Figure 5:
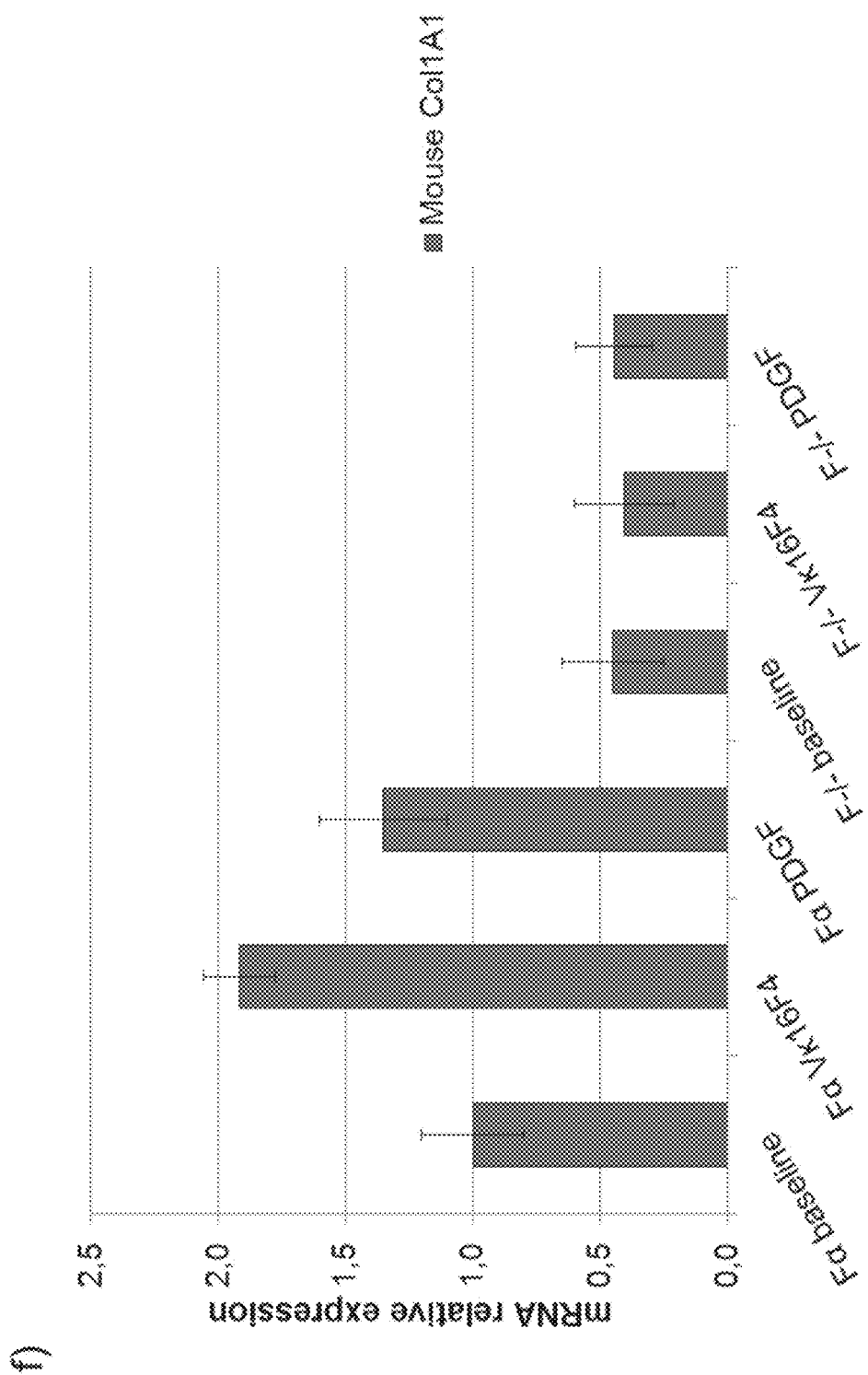

The common VH PAM chain cDNA sequence was alternatively paired with each of the four VL chain cDNA sequences described above, and sub-cloned into an expression vector containing the complete sequence of human IgG1 constant region, including the Fc. These four constructs were engineered and stably transfected into CHO eukaryotic cells to produce four distinct recombinant human monoclonal IgG, designated as Vk13B8, Vlambda13B8, Vk16F4 and Vlambda16F4 rHumaab, generated by the restricted PDGFR auto-reactive immune repertoire of this SSc patient. The same antibody engineering process was applied to VH and VL ROM cDNA sequences, in order to obtain four additional recombinant human monoclonal IgG, designated as VH1-Vk13B8, VH2-Vk13B8, VH1-Vlambda1, and VH2-Vlambda1, whose stable production and characterization is in progress. To characterize binding and agonistic properties of the anti-PDGFR rHumaab generated, immunoprecipitation and immunoblotting were performed. The results indicated that Vk13B8, Vk16F4 and Vlambda16F4 rHumaab specifically bound to PDGFR alpha contained in normal human fibroblast extracts, whereas, surprisingly, Vlambda13B8 rHumaab did not immunoprecipitate PDGFR alpha (FIG. 5a). As expected, rHumaab carrying the 13B8 VL chains did not stimulate human fibroblasts, whereas the rHumaab carrying the 16F4 VL chains induced ROS production and ERK phosphorylation in human fibroblasts (FIG. 5b,c). However, Vk16F4 was the only rHumaab stimulating an increase of type I collagen gene transcription in normal human fibroblasts (FIG. 5d). Unlike PDGF-BB, that induced collagen genes only up to 6 hours, Vk16F4 maintained collagen stimulation stable up to 24 hours (FIG. 5e), thus recapitulating the main properties previously attributed to total IgG purified from serum of SSc patients. To demonstrate that type I collagen gene induction in fibroblasts was the result of a specific binding of Vk16F4 rHumaab to PDGFR alpha, F alpha and F−/− cells were treated in parallel with Vk16F4 rHumaab. In this experimental setting, type I collagen gene up-regulation was observed only in F alpha cells, confirming that PDGFR alpha expression is specifically required by Vk16F4 rHumaab to exert its agonistic activity (FIG. 5f). In addition, preliminary results suggested that Vk16F4 rHumaab is able to stimulate proliferation and migration of human smooth muscle cells, another cell type involved in key pathogenic processes leading to SSc phenotype.

Figure 6:
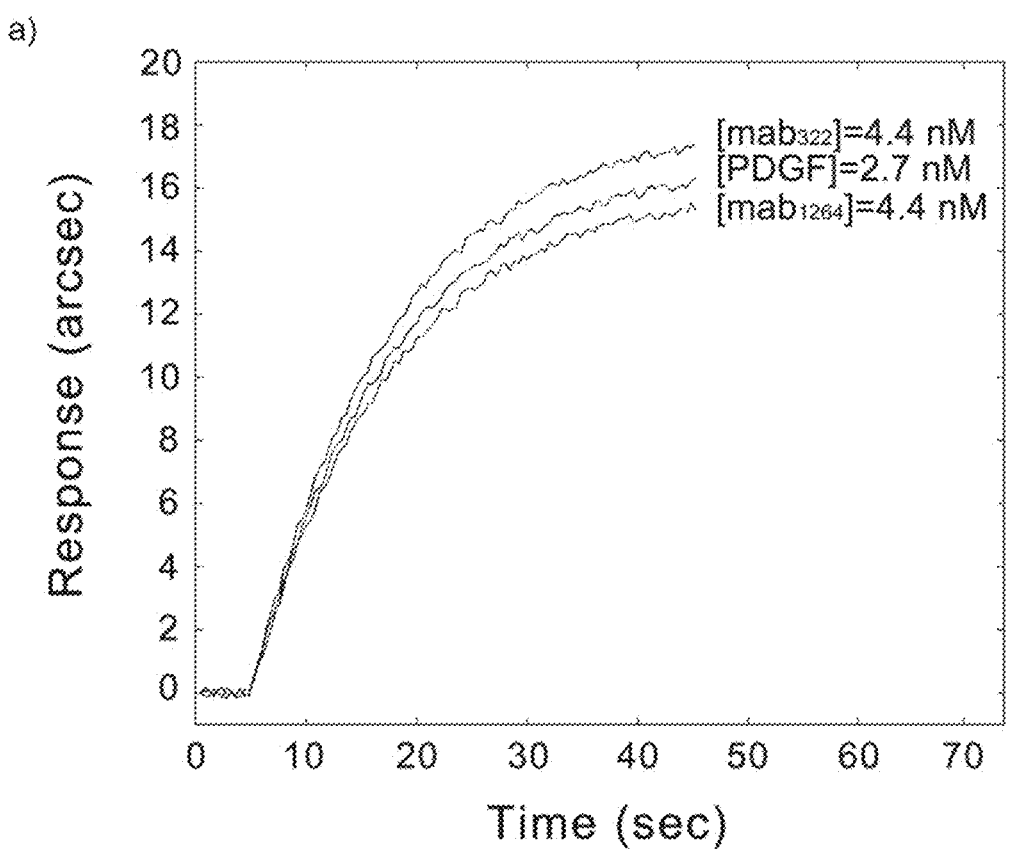
FIG. 6 Binding kinetics of anti-PDGFR alpha rHumaab and PDGF-BB to PDGFR. Each panel shows the sensortraces obtained by probing immobilized His-tagged PDGFR alpha with the indicated ligands used at different concentrations. (a) Human PDGF-BB and mabs 322 and 1264, commercial mouse monoclonal antibodies binding to conformational epitopes of human PDGFR alpha; (b) human PDGF-BB; (c-e) Vk13B8, Vk16F4, Vlambda16F4 compared with non-binding Vlambda13B8 rHumaab; (d) 10 nM Vk16F4 bound to PDGFR alpha saturated with molar excess of Vk13B8; (f) Vk13B8, but not Vk16F4, bound to PDGFR alpha saturated with molar excess of PDGF-BB. Asterisks indicate addition of rHumaab after saturation of PDGFR alpha with Vk13B8 (d) and PDGF (f).
Figure 6:
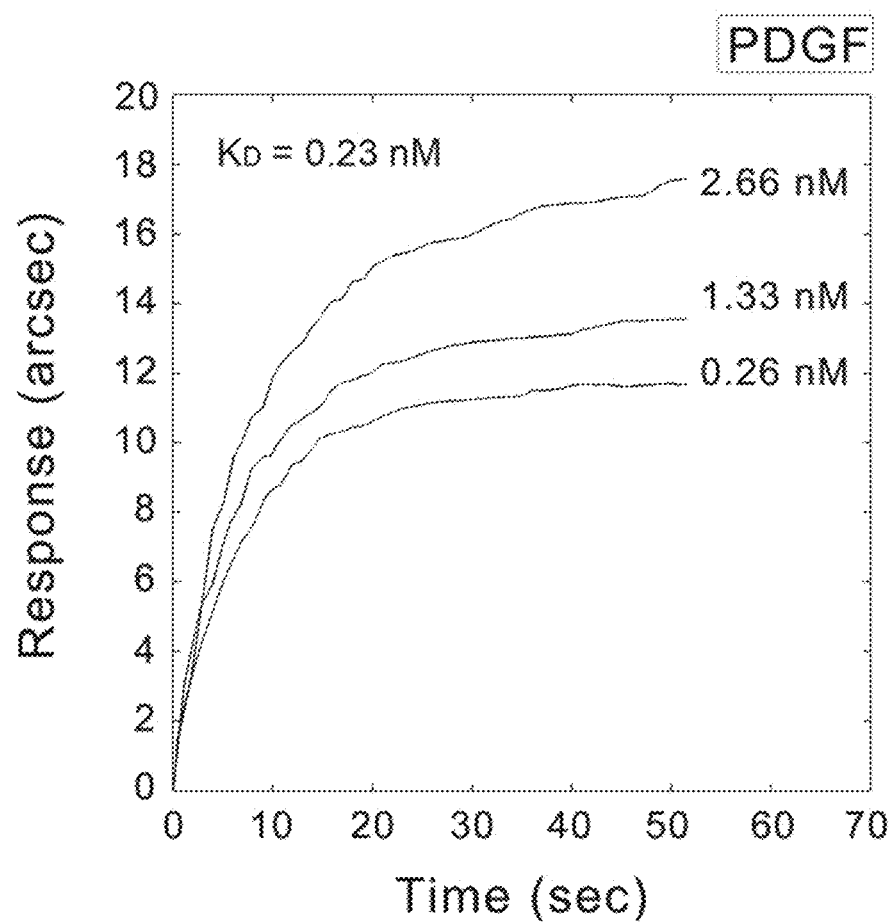
Figure 6:
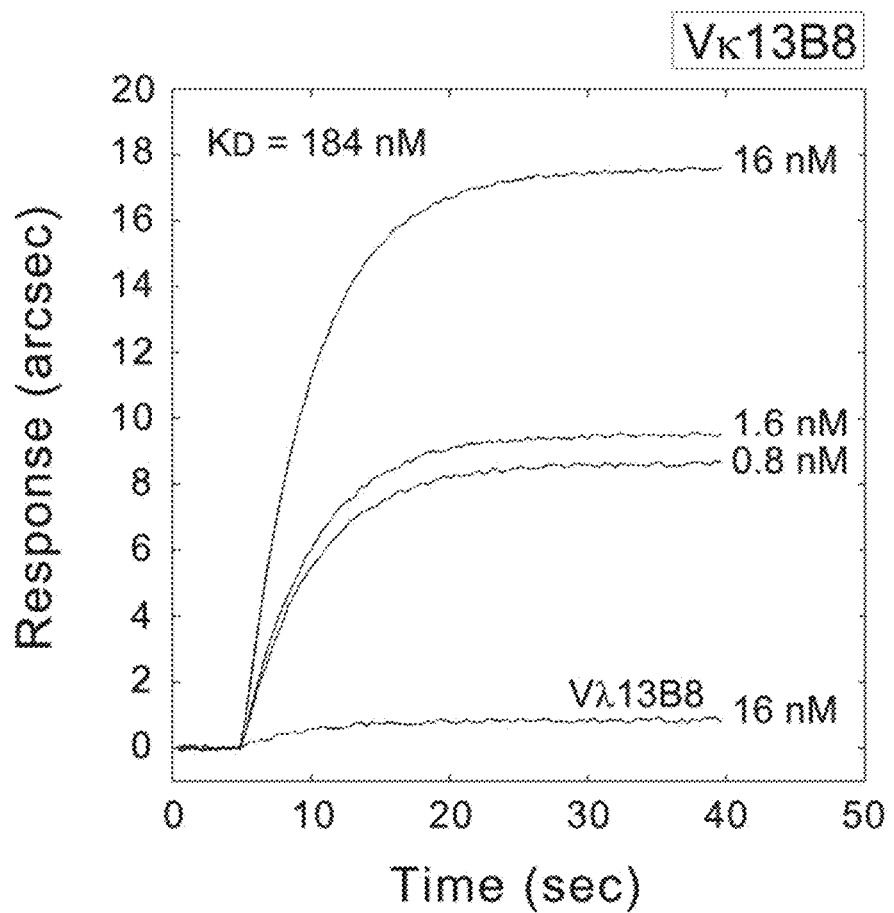
Figure 6:
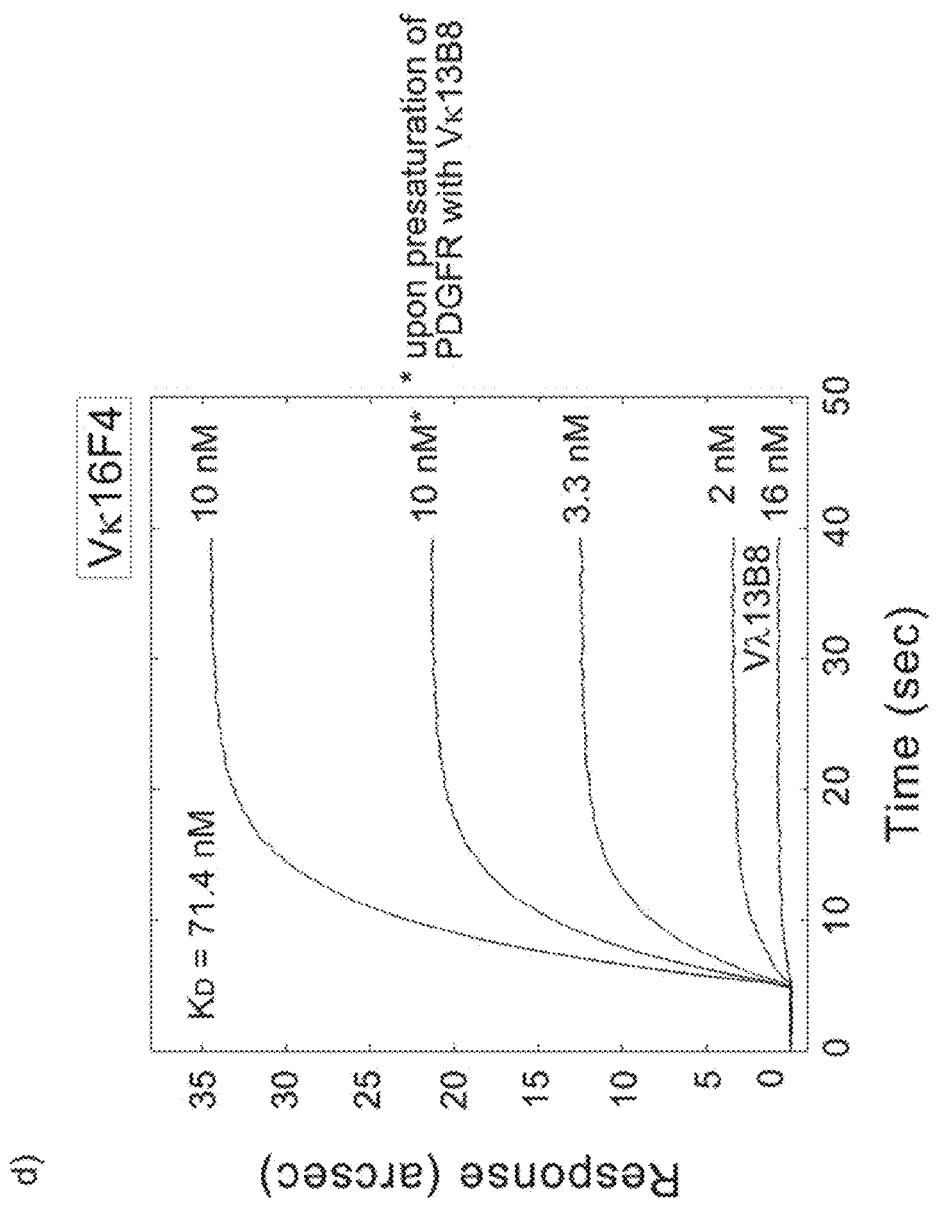
Figure 6:
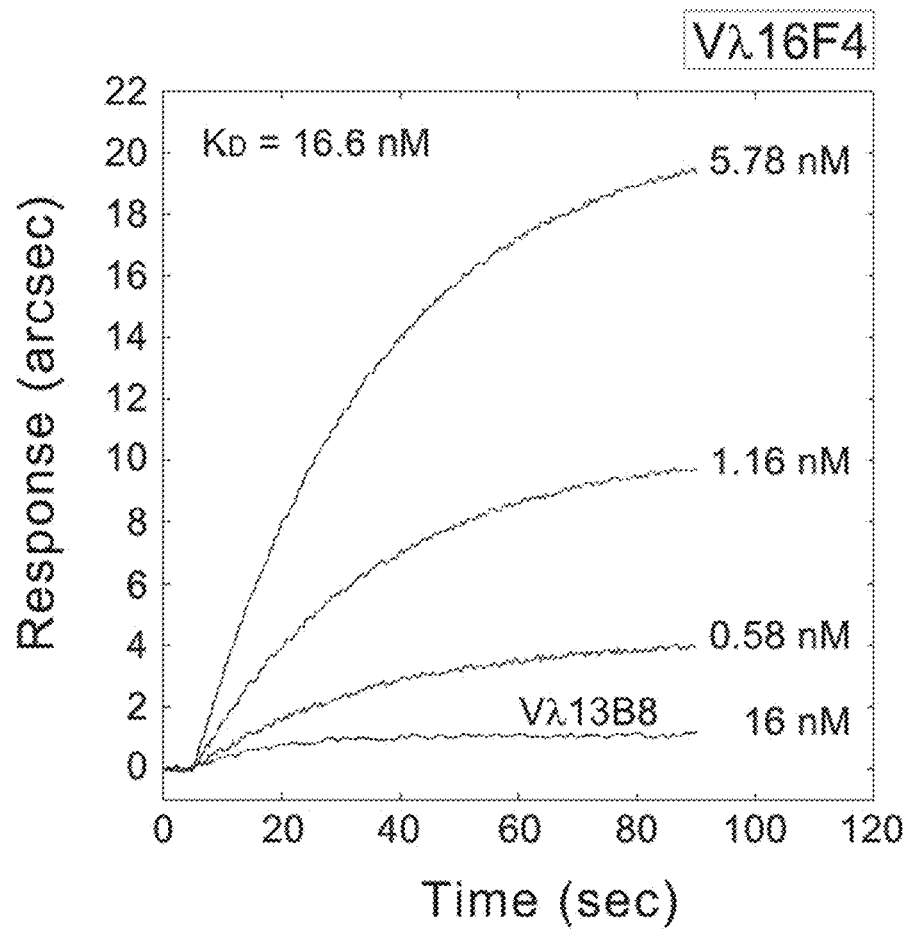
Figure 6:
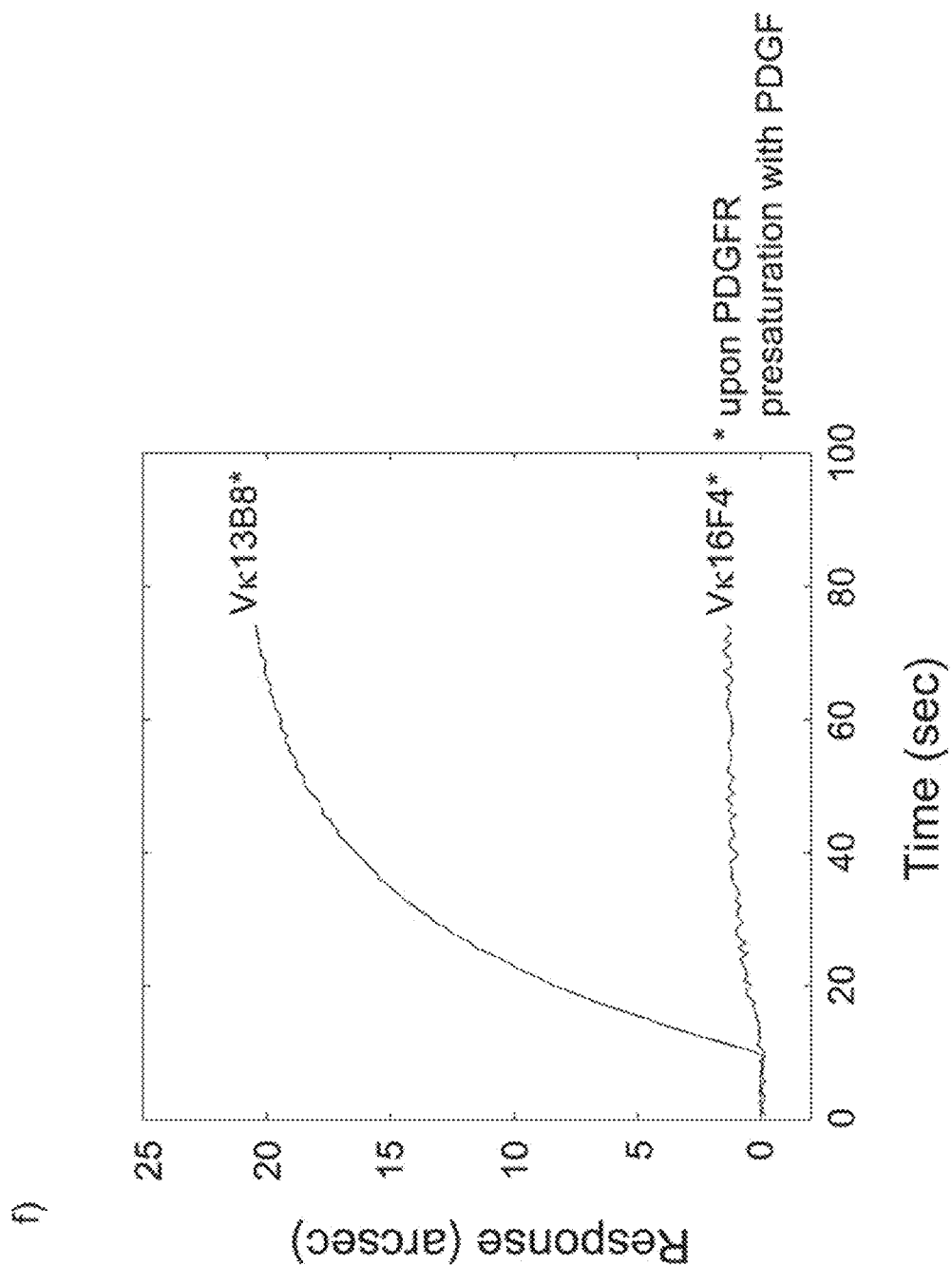

A detailed characterization of rHumaab interaction with human PDGFR alpha was performed on an optical biosensor, using as a molecular bait a homemade truncated conformer of this receptor containing the complete extracellular and transmembrane regions joined to a poly-histidine tail (HIS tag) replacing part of the intracellular domain, and serving both as an anchor to the biosensor surface and as a spacer. Preservation of proper folding of the immobilized receptor into a naïve-like conformation was verified by monitoring the interaction with its natural binding partner (PDGF-BB) and with two mouse monoclonal antibodies specific for conformational PDGFR alpha epitopes (FIG. 6a). Using this approach, both kinetics and equilibrium parameters of the interaction between PDGF-BB, each rHumaab and PDGFR alpha were determined. PDGF-BB displayed the highest affinity (Kd=0.23 nM) (FIG. 6b), with Vk13B8, Vk16F4 and Vlambda16F4 rHumaab affinity also lying in the nanomolar range (Kd=184 nM, 71.4 nM and 16.6 nM, respectively) (FIG. 6c-e). Vlambda13B8 rHumaab did not bind to PDGFR alpha, as anticipated by the immunoprecipitation data (FIG. 6c-e). Additionally, the analysis of association and dissociation rate constants for soluble ligands binding to PDGFR alpha, further defined the mechanistic properties of the macromolecular recognition process. In detail, the observed differences in terms of affinity between PDGF-BB and rHumaab could be mostly attributable to the faster association phase ($kass=3 \cdot 10^7$ $M^{-1}s^{-1}$) of PDGF-PDGFR complexes compared to rHumaab-PDGFR complexes (all kass values ranging between $1.8 \cdot 10^6$ and $2.8 \cdot 10^6$ $M^{-1}s^{-1}$). Conversely, differences in equilibrium constants among rHumaab were reflected by corresponding differences in dissociation rate constants (kdiss=, 0.035 $s^{-1}$, 0.02 $s^{-1}$, and 0.003 $s^{-1}$, respectively for Vk13B8, Vk16F4 and Vlambda16F4).

PDGFR Epitope Mapping

To draw a map of the PDGFR alpha epitopes recognized by the rHumaab, competitive binding experiments were performed on the optical biosensor platform, where the surface of immobilized HIS-tagged PDGFR alpha was saturated with PDGF-BB prior to the addition of each rHumaab. The results showed that i) binding of Vk16F4 (but not of Vk13B8) rHumaab was prevented by pre-saturation of the immobilized receptor with PDGF-BB, indicating that the epitopes bound by PDGF and Vk16F4 at least partly overlap (FIG. 6f), and that ii) Vk13B8 (non-agonistic) and Vk16F4 (agonistic) rHumaab likely recognize different PDGFR epitopes. The observation that pre-saturation with the Vk13B8 rHumaab only marginally interfered with Vk16F4 binding to the immobilized PDGFR alpha strengthened this assumption (FIG. 6d).

Figure 7:
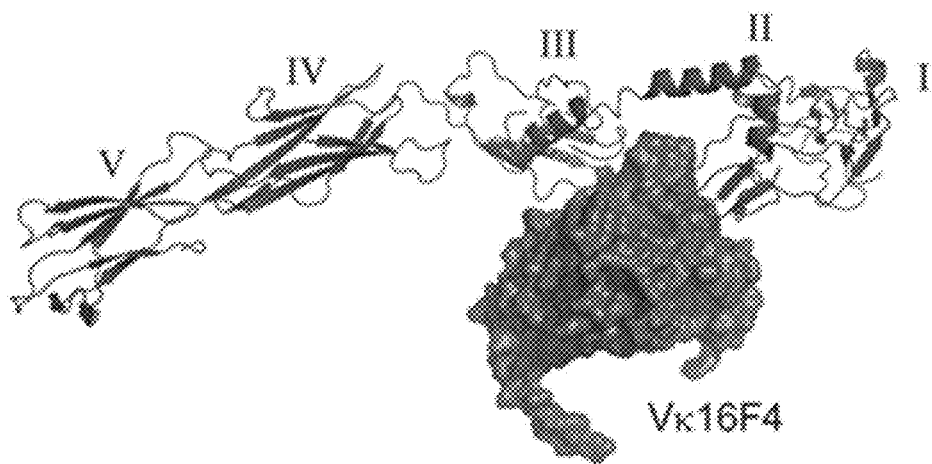
FIG. 7 PDGFR alpha epitope mapping. On the left are shown molecular docking models of rHumaab Fabs and monomeric PDGF-BB with the extracellular region of monomeric PDGFR alpha (Ig-like domains are labeled I to V, from the N-terminus to the transmembrane domain). On the right side of each model, the aminoacid sequence of the N-terminal three extracellular domains of PDGFR alpha is shown. rHumaab and PDGF epitopes predicted by molecular docking (md) are evidenced by bars, whereas epitopes identified through library screening (ls) are underlined. (A) Vκ13B8 epitope: aminoacid (aa) residues 33-43 (md), 36-50 (ls). (B) Vκ16F4 epitope: aa residues 141-144 (md), 141-152 (ls); 181-183 (md), 172-186 (ls); 294-301 (md), 294-301 (ls). (C) PDGF-BB epitope: aa residues 101-105 (md), 92-106 (ls); 141-144 (md); 181-183 (md), 169-183 (ls); 295-297 (md). (D) Vlambda16F4 epitope: aa residues (md, awaiting ls confirmation) 42-45; 83-94; 199-205.
Figure 8:
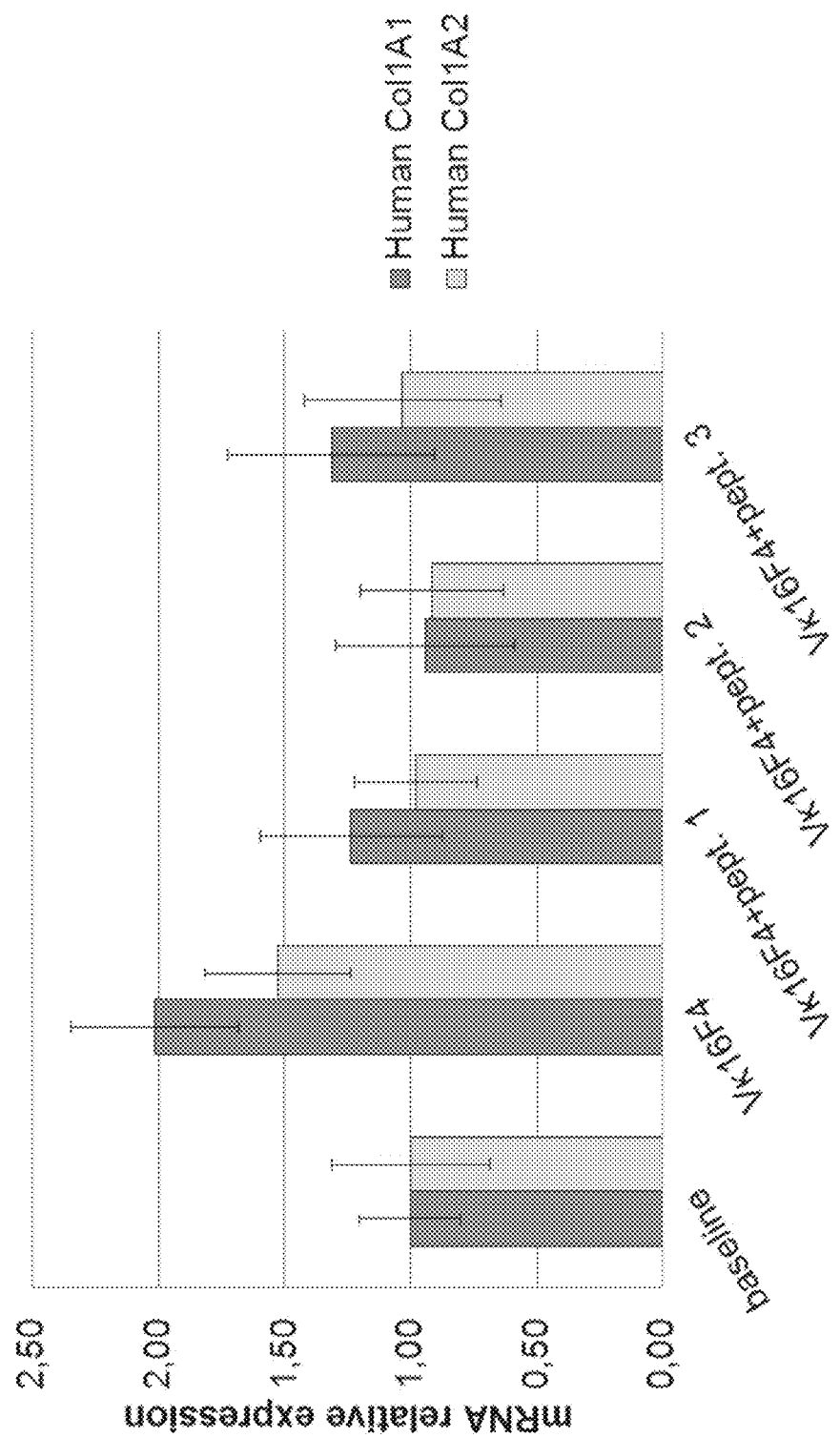
FIG. 8 Inhibition of Vk16F4 rHumaab agonistic activity. Vk16F4 rHumaab was pre-incubated with molar excess (100×) of each of the three polypeptides corresponding to its discontinuous epitope prior to collagen gene stimulation assay. Peptides were numbered from 1 to 3 following the amino acid sequence from the $NH_2$ terminus to the COOH—terminus (see FIG. 5, second panel from the top, on the right). aa sequences: peptide 1 ac-VIVEDDDSAIIPCRTTD-conh2 (aa. 138-154 of SEQ ID No. 1), peptide 2 ac-VVPASYD-SRQGFNGTFTVGPYICE-conh2 (aa. 167-190 of SEQ ID No. 1), peptide 3 ac-CAARQATREVKEMKKVT-conh2 (aa. 290-306 of SEQ ID No. 1). Collagen gene levels were measured by qPCR as described above.

To further define the PDGFR alpha binding sites of each rHumaab Fab monovalent fragment and of PDGF-BB, homology modeling of these structures and subsequent in silico molecular docking between PDGFR alpha and PDGF-BB or individual rHumaab Fabs were performed. Using this method, a predicted map of the PDGFR epitopes bound by the physiological ligand PDGF-BB or by each rHumaab paratope was obtained (FIG. 7). PDGF-BB was shown to bind to a discontinuous epitope constituted by four discrete aminoacid stretches lying between the second and the third Ig-like extracellular domains of PDGFR alpha. This topology is consistent with previous studies (Shim A H et al. Proc Natl Acad Sci USA. 2010; 107(25):11307-12) reporting that the second and third PDGFR alpha extracellular domains are required for PDGF binding to its receptor. The agonistic Vk16F4 rHumaab was shown to bind to a discontinuous epitope largely overlapping with that of PDGF, but spanning longer aminoacid stretches within the second and third PDGFR alpha extracellular domains, supporting the results of competitive binding experiments. Conversely, the predicted epitope of the non-agonistic Vk13B8 rHumaab encompassed a single linear aminoacid sequence within the first PDGFR alpha extracellular domain. Vlambda16F4 rHumaab was shown to bind to a discontinuous epitope formed by three PDGFR alpha sequences, two comprised in the first extracellular domain and one in the second (FIG. 7). To corroborate these in silico predictive data, an aptly designed peptide library encompassing the three N-terminal extracellular domains of PDGFR alpha was generated and probed with PDGF-BB and each rHumaab. The results showed a remarkable correspondence between the predicted (in silico) and the actual (in vitro) PDGFR alpha epitopes bound by each rHumaab and by the natural ligand (FIG. 7). To assess the individual contribution of the three peptides composing the conformational epitope recognized by the agonistic Vk16F4 rHumaab, three polypeptides corresponding to these sequences were generated and pre-incubated in molar excess with Vk16F4 before performing stimulation experiments with human fibroblasts. The results demonstrated that pre-incubation with either polypeptides partially or completely prevented Vk16F4-mediated stimulation of collagen gene transcription (FIG. 8), suggesting that accessibility of Vk16F4 rHumaab to each component of its epitope is required for Vk16F4-induced intracellular signaling leading to increased transcription of type I collagen gene.

METHODS

Isolation and Immortalization of Memory B Cells from Peripheral Blood

Use of human material was approved by the Institutional Ethical Committee of the Università Politecnica delle Marche, Ancona, Italy, and consent was obtained from all subjects pertecipating to this study. IgG-positive, CD22-positive memory B cells were purified by magnetic selection (Miltenyi Biotech) from peripheral blood mononuclear cells (PBMC) of patients affected by SSc. Cells were immortalized using Epstein-Barr virus (EBV) as described previously (Funaro A et al. BMC Biotechnology 2008; 8: 85) and directly seeded (5 cells/well) in 96-well plates (Nunc) in the presence of irradiated allogenic PBMC in complete RPMI 1640 medium (Sigma Aldrich) supplemented with 10% fetal calf serum FCS (HyClone), 50 units/ml penicillin, 50 μg/ml streptomycin (Sigma Aldrich), 2 mM L-alanyl-L-glutamine (Sigma Aldrich). Following 2 weeks of culture, B cell supernatants were screened by immunofluorescence and flow cytometry. Selected B cell cultures were expanded and adapted to grow in serum-free medium (Hybridoma-SFM, Gibco).

Immunofluorescence and Flow Cytometry

Adherent mouse embryo fibroblasts (F alpha and F−/−) were suspended for flow cytometry by incubation with 0.75 mM EDTA, washed and incubated for 40 minutes at 4° C. with the B cell supernatants (50 μl/$10^5$ cells), then washed with PBS and incubated with F(ab')$_2$-Rabbit anti-Human IgG-FITC (Jackson ImmunoResearch) 30 minutes at 4° C. Fluorescence was analyzed by means of a FACSCalibur flow cytometer using CellQuest software (Becton Dickinson). Background mAb binding was estimated by means of isotype-matched negative control human monoclonal antibody.

Immunoprecipitation and Immunoblotting

Immunoprecipitating antibodies were individually incubated for 4 hours at 4° C. with an aliquot of 100 micrograms of total protein from human fibroblast extract. The reaction mixture was adjusted to a final volume of 500 microliters with assay buffer (PBS, 1% Nonidet P-40, 0.5% sodium deoxycholate, 1 mM PMSF). Rabbit anti-PDGFR alpha antibody and rabbit IgG (Santa Cruz), IgG purified from EBV-transformed B cell culture supernatants and rHumaab were used at 10 micrograms/ml, total IgG purified from serum of SSc patients and healthy subjects at 200 micrograms/ml. Then, 20 microliters agarose-Protein A/G (Santa Cruz) were added to the antibody-cell extract mixture and incubated overnight under rotation at 4° C. After centrifugation and extensive washing, immunoprecipitates were suspended in 20 microliters of loading buffer (150 mM Tris-HCl, pH 6.8/6% SDS/ 0.3% bromophenol blue/30% glycerol) and heated to 100° C. for 10 minutes prior to immunoblotting with a commercial rabbit anti-PDGFR alpha antibody (Santa Cruz).

Functional Assays

Human skin fibroblasts were cultured and used within the fifth passages. When cell cultures reached sub-confluence in 60 mm Petri dishes, medium containing 10% FCS was replaced with fresh medium containing 0.2% FCS. After 24 hours, PDGF-BB (15 ng/ml), TGF-beta (2 ng/ml) and rHumaab (10 micrograms/ml) were added individually. For each experimental time point, a duplicate cell culture dish was kept in 0.2% FCS medium without stimulation to rule out any confounding effects due to low serum conditions. For rHumaab, a duplicate cell culture dish was treated with equal volume of PBS (vehicle control). For inhibition of Vk16F4 rHumaab agonistic activity, longer versions (extended with some residues at N- and C-terminus) of the three peptides composing the Vk16F4 epitope were synthesized (HPLC purity >95%). To increase the solubility, ac- and -conh2 groups were added at N- and C-terminus, respectively. Peptides were individually incubated in molar excess (100×) with Vk16F4 rHumaab for 1 hour at 37° C. and used to stimulate human fibroblasts, as described below. p-ERK and ROS assays were performed as described (Baroni S S, NEJM 2006). For collagen gene quantification, total RNA was extracted from human and mouse fibroblasts at baseline and after 1 hour stimulation with the reagents indicated above, using Aurum total RNA mini Kit (Bio-Rad), which included DNase treatment. Quantification and quality control of RNA were performed by spectrophotometer (Nanodrop; Thermo Scientific); the purity of RNA templates measured by 260/280 nm ratio was in the 1.8-2.1 range. One microgram RNA was reverse transcribed with iScript cDNA synthesis Kit (Bio-Rad). Expression levels of human Col1A1 and Col1A2 and mouse Col1A1 genes were detected by real-time PCR, using iCycler thermal Cycler (Bio-Rad) with iQ SYBR Green Supermix (Bio-Rad) and the following primers: HuCol1A1 5'-agggccaagacgaagacatc-3'(fw) (SEQ ID No. 13), 5'-agatcacgtcatcgcacaaca-3'(rev) (SEQ ID No. 14); HuCol1A2 5'-aggtcaaacaggagcccgtggg-3'(fw) (SEQ ID No. 15), 5'-gcacctgggaagcctggaggg-3'(rev) (SEQ ID No. 16); MoCol1A1 5'-taggccattgtgtatgcagc-3'(fw) (SEQ ID No. 17), 5'-acatgttcagctttgtggacc-3'(rev) (SEQ ID No. 18). PCR conditions were: 95° C. for 30 s, 95° C. for 15 s (40 cycles), 58° C. for 30 s, 55° C. for 60 s. Human reference genes used for normalization were the glyceraldehyde 3' phosphate dehydrogenase (GAPDH) gene: 5'-tgcaccaccaactgcttagc-3'(fw) (SEQ ID No. 19), 5'-tgggatttccattgatgacaagc-3'(rev) (SEQ ID No. 20) and the 18S ribosomal RNA gene: 5'-tccccatgaacgaggaattc-3'(fw) (SEQ ID No. 21), 5'-gtgtacaaagggcagggactt-3' (rev) (SEQ ID No. 22). Mouse reference genes used for normalization were the 18S ribosomal RNA gene: 5'-agtccctgcctttgtacaca-3'(fw) (SEQ ID No. 23), 5'-cgatccgagggcctcacta-3'(rev) (SEQ ID No. 24) and the mouse cyclophilin A gene: 5'-cagtgctcagagctcgaaagt-3'(fw) (SEQ ID No. 25), 5'-gtgttcttcgacatcacggc-3'(rev) (SEQ ID No. 26).

Analysis of Human Immunoglobulin Gene Repertoire

RNA was extracted from each selected memory B cell lines and reverse-transcribed into cDNA by Omniscript RT Kit (Qiagen). cDNA was used as PCR template with primers designed to amplify human rearranged IgG and IgM variable (V) and constant (C) heavy (H) and light (L) chain genes (Welschof M. et al. Journal of Immunological Methods 1995; 179: 203-214). Amplified H and L chain variable regions were sequenced by TOPO TA Cloning Kit (Invitrogen). For qPCR of CDR3 genes, total RNA was prepared from 5 ml of fresh peripheral blood in EDTA using QIAamp RNA blood mini KIT (Qiagen). One microgram RNA was reverse transcribed either with iScript cDNA synthesis Kit (Bio-Rad), or with GoScript RT Kit (Promega) and IgG-specific reverse primers VH2: 5'-caggtgcagctgcaggagtc-3'(SEQ ID No. 27), and VK1/4: 5'-gacatccagatgacccagtctcc-3' (SEQ ID No. 28). Expression levels of VH PAM and Vk16F4 CDR3 genes were detected by real-time PCR using iCycler thermal Cycler (Bio-Rad) with iQ SYBR Green Supermix (Bio-Rad) and the following primers: VH PAM 5'-ggaaccaccaactacagc-3'(fw) (SEQ ID No. 29), 5'-gccccagatttcaaaagaatc-3'(rev) (SEQ ID No. 30); Vk16F4 5'-tcctttactgggcatctacc-3'(fw) (SEQ ID No. 31), 5'-cccttggccgaacgtctt-3'(rev) (SEQ ID No. 32). PCR conditions were 95° C. for 30 s, 95° C. for 15 s (45 cycles), 58° C. for 60 s, and 55° C. for 60 s. Reference genes used for normalization were GAPDH gene, Ck gene: 5'-tcggtcactctgttcccg-3'(fw) (SEQ ID No. 33), 5'-atctgccttccaggccac-3'(rev) (SEQ ID No. 34), C1 gene: 5'-tggctgcaccatctgtcttc-3'(fw) (SEQ ID No. 35), 5'-ctatcccagagaggccaaag-3'(rev) (SEQ ID No. 36).

Generation of rHumaab

The unique VH and the four different VL chain sequences amplified in the three PDGFR alpha auto-reactive memory B cell lines were alternatively paired to replace VH and VL chains of antibody b12 (Burton D R et al. Science 1994; 266: 1024-1027). generating four discrete human IgG1 constructs. First, VH and VL sequences were each fused with the respective leader peptide sequences by using a three-step overlap extension PCR (Moroncini G et al. Proc Natl Acad Sci USA. 2004; 101(28): 10404-9), then independently inserted into the XbaI-SacI and HindIII-EcoRI restriction sites of pDR12 vector containing the parental human IgG1 constant chain genes, including the Fc sequence. Upon sequencing, the four constructs were stably transfected into CHO cells, and the best transfectants were selected based on human IgG production levels (ELISA) and adapted to grow in serum-free medium. Cell cultures were expanded in bioreactors (Integra) and secreted rHumaab were purified from supernatants by two-step (protein A affinity+size exclusion) chromatography (Pierce).

Generation of His-Tagged PDGFR cDNA encoding aminoacids 1-834 of human PDGFR alpha was inserted in the pcDNA V5 HIS A vector (Invitrogen), in order to fuse the COOH— terminal of the protein with a 6× histidine tag. Upon sequencing, the construct was stably transfected into HeLa cells and the best transfectants were selected based on PDGFR alpha expression levels (FACS) and expanded. His-tagged PDGFR alpha was purified from cellular lysates by HiTrap chelating columns (Amersham) and dialyzed to remove imidazole traces. Presence of a single His-tagged PDGFR alpha product in eluted fractions was evaluated by immunoblotting with specific anti-PDGFR alpha (R&D Biosystems) and anti-histidine (Sigma-Aldrich) monoclonal antibodies.

Binding Assays

Binding assays were performed on a IAsys plus biosensor. The carboxylate surface was equilibrated with PBS buffer, and activated by addition of an equimolar mixture of N-hydroxysuccinimide and N-ethyl-N-(dimethylaminopropyl) carbodiimide hydrochloride following the standard procedure (Davies, R J et al. Academic Press: San Diego, 1994).

Next, His-tagged PDGFR alpha (200 micrograms/mL) was incubated over the surface for 20 min, and free carboxylic sites on the sensor surface were deactivated by injection of 1M ethanolamine, pH 8.5. Finally, the surface was re-equilibrated with PBS. rHumaab and PDGF-BB were added at different concentrations, and association kinetics were followed up to equilibrium, whereas dissociation steps and surface regeneration were performed by addition of fresh buffer, each time assessing the baseline recovery prior to any new addition of ligand. Kinetic and equilibrium parameters were derived from global fit of raw data both to mono- and bi-exponential models (Cuccioloni M et al. J Lipid Res 2011; 52 (5): 897-907).

Homology Modeling and Molecular Docking

Swiss-Pdb Viewer software (version 4.01) was used to create project files submitted to the server with default parameters settings (BLAST search P value <0.00001 and global degree of sequence identity SIM >25%). Moreover, 2e9wA, 2e9wB and 2ec8A were selected as structure templates for PDGFR alpha sequence and 1HZH was selected as structure templates for Fab sequence. PDGFR query sequences were obtained from UniProt Knowledgebase (http://beta.uniprot.org/). Rigid protein-protein molecular docking between homology-modelled rHumaab Fabs or PDGF-BB (pdb-ID: 1PDG) (Oefner C et al. EMBO J. 1992; 11(11): 3921-6) and PDGFR alpha was carried out uploading the pdb files on ClusPro 2.0 server and setting DOT 1.0 as docking program, a clustering radius of 5 Å, electrostatic hits of 1500 and 30 final resulting structures.

Generation and Screening of PDGFR Peptide Library

A library of peptides spanning the first three extracellular domains of PDGFR alpha was synthesized by Pepscan Presto, Lelystad, The Netherlands. Up to 35-mer peptides (250 single-looped and 250 double-looped peptides) were synthesized on chemical scaffolds in order to reconstruct conformational epitopes, using Chemically Linked Peptides on Scaffolds (CLIPS) technology (Timmerman et al.. J. Mol.

Recognit. 2007; 20: 283-99). Alanine-scans were included in the library. Binding of rHumaab and PDGF-BB to each peptide was tested by PEPSCAN-based ELISA (Slootstra et al. Molecular Diversity 1996; 1: 87-96).

Statistical Analysis

Relative quantification of target genes between samples was calculated by the $2^{-\Delta\Delta Ct}$ method using the program iQ5 (Bio-Rad). For binding assays, monophasic time courses were always reported upon addition of soluble rHumaab (the validity of the monophasic model in fitting each time course was assessed according to a standard F-test procedure, with the biphasic model being statistically nonsignificant at 95% confidence) (Bevington P R and Robinson D K. McGraw-Hill Book Company, New York. 1992).

The invention claimed is:

1. A peptide consisting of amino acid residues (aa) 36-306 of SEQ ID NO: 1, or subsequences thereof, wherein said peptide is a discontinuous epitope for anti-hPDGFR alpha agonistic auto-antibodies.

2. The peptide according to claim 1 consisting of aa 172-186, aa 141-152, and aa 294-301 of SEQ ID NO: 1.

3. The peptide according to claim 1 consisting of aa 167-190, aa 138-154, and aa 290-306 of SEQ ID NO: 1.

4. The peptide according to claim 1 consisting of aa 42-45, aa 83-94 and aa 199-205 of SEQ ID NO: 1.

5. The peptide according to claim 1 consisting of aa 172-486, and/or aa 141-152 and/or aa 294-301 of SEQ ID NO: 1.

6. The peptide according to claim 1 consisting of aa 167-190, and/or aa 138-154, and/or aa 290-306 of SEQ ID NO: 1.

7. The peptide according to claim 1 consisting of aa 42-45, and/or aa 83-94, and/or an 199-205 of SEQ ID NO: 1.

8. The peptide according to claim 1 comprising aa 172-486, and/or aa 141-152, and/or 294-301 of SEQ ID NO: 1.

9. The peptide according to claim 1 comprising aa 42-45 and/or aa 83-94 and/or aa 199-205 of SEQ ID NO: 1.

10. The peptide according to claim 1 consisting of amino acid residues aa 36-306 of SEQ ID NO: 1.

* * * * *

UNITED STATES PATENT AND TRADEMARK OFFICE
CERTIFICATE OF CORRECTION

PATENT NO.         : 9,150,634 B2
APPLICATION NO.    : 13/812764
DATED              : October 6, 2015
INVENTOR(S)        : Gianluca Moroncini et al.

Page 1 of 1

It is certified that error appears in the above-identified patent and that said Letters Patent is hereby corrected as shown below:

In the Claims:

Claim 8 on column 36, line 32-33 Approximately should read as follows:

--8. The peptide according to claim 1 comprising aa 172-186, and/or aa 141-152, and/or 294-301 of SEQ ID NO: 1.--

Signed and Sealed this
Fifteenth Day of March, 2016

Michelle K. Lee
*Director of the United States Patent and Trademark Office*

SEQUENCE LISTING

```
<160> NUMBER OF SEQ ID NOS: 36

<210> SEQ ID NO 1
<211> LENGTH: 1089
<212> TYPE: PRT
<213> ORGANISM: Homo sapiens

<400> SEQUENCE: 1

Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320
```

```
Phe Ser Gln Leu Glu Ala Val Asn Leu His Glu Val Lys His Phe Val
                325                 330                 335
Val Glu Val Arg Ala Tyr Pro Pro Arg Ile Ser Trp Leu Lys Asn
        340                 345                 350
Asn Leu Thr Leu Ile Glu Asn Leu Thr Glu Ile Thr Thr Asp Val Glu
            355                 360                 365
Lys Ile Gln Glu Ile Arg Tyr Arg Ser Lys Leu Lys Leu Ile Arg Ala
        370                 375                 380
Lys Glu Glu Asp Ser Gly His Tyr Thr Ile Val Ala Gln Asn Glu Asp
385                 390                 395                 400
Ala Val Lys Ser Tyr Thr Phe Glu Leu Leu Thr Gln Val Pro Ser Ser
                405                 410                 415
Ile Leu Asp Leu Val Asp His His Gly Ser Thr Gly Gly Gln Thr
            420                 425                 430
Val Arg Cys Thr Ala Glu Gly Thr Pro Leu Pro Asp Ile Glu Trp Met
            435                 440                 445
Ile Cys Lys Asp Ile Lys Lys Cys Asn Asn Glu Thr Ser Trp Thr Ile
        450                 455                 460
Leu Ala Asn Asn Val Ser Asn Ile Ile Thr Glu Ile His Ser Arg Asp
465                 470                 475                 480
Arg Ser Thr Val Glu Gly Arg Val Thr Phe Ala Lys Val Glu Glu Thr
                485                 490                 495
Ile Ala Val Arg Cys Leu Ala Lys Asn Leu Leu Gly Ala Glu Asn Arg
            500                 505                 510
Glu Leu Lys Leu Val Ala Pro Thr Leu Arg Ser Glu Leu Thr Val Ala
        515                 520                 525
Ala Ala Val Leu Val Leu Leu Val Ile Val Ile Ile Ser Leu Ile Val
            530                 535                 540
Leu Val Val Ile Trp Lys Gln Lys Pro Arg Tyr Glu Ile Arg Trp Arg
545                 550                 555                 560
Val Ile Glu Ser Ile Ser Pro Asp Gly His Glu Tyr Ile Tyr Val Asp
                565                 570                 575
Pro Met Gln Leu Pro Tyr Asp Ser Arg Trp Glu Phe Pro Arg Asp Gly
            580                 585                 590
Leu Val Leu Gly Arg Val Leu Gly Ser Gly Ala Phe Gly Lys Val Val
        595                 600                 605
Glu Gly Thr Ala Tyr Gly Leu Ser Arg Ser Gln Pro Val Met Lys Val
            610                 615                 620
Ala Val Lys Met Leu Lys Pro Thr Ala Arg Ser Ser Glu Lys Gln Ala
625                 630                 635                 640
Leu Met Ser Glu Leu Lys Ile Met Thr His Leu Gly Pro His Leu Asn
                645                 650                 655
Ile Val Asn Leu Leu Gly Ala Cys Thr Lys Ser Gly Pro Ile Tyr Ile
            660                 665                 670
Ile Thr Glu Tyr Cys Phe Tyr Gly Asp Leu Val Asn Tyr Leu His Lys
        675                 680                 685
Asn Arg Asp Ser Phe Leu Ser His His Pro Glu Lys Pro Lys Lys Glu
            690                 695                 700
Leu Asp Ile Phe Gly Leu Asn Pro Ala Asp Glu Ser Thr Arg Ser Tyr
705                 710                 715                 720
Val Ile Leu Ser Phe Glu Asn Asn Gly Asp Tyr Met Asp Met Lys Gln
                725                 730                 735
```

```
Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
            755                 760                 765

Lys Lys Lys Ser Met Leu Asp Ser Glu Val Lys Asn Leu Leu Ser Asp
            770                 775             780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Arg Asp Ile Met His Asp Ser Asn
            835                 840                 845

Tyr Val Ser Lys Gly Ser Thr Phe Leu Pro Val Lys Trp Met Ala Pro
            850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
                900                 905                 910

Tyr Arg Met Ala Lys Pro Asp His Ala Thr Ser Glu Val Tyr Glu Ile
            915                 920                 925

Met Val Lys Cys Trp Asn Ser Glu Pro Glu Lys Arg Pro Ser Phe Tyr
            930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Arg Val Asp Ser Asp Asn Ala Tyr Ile Gly Val Thr
                980                 985                 990

Tyr Lys Asn Glu Glu Asp Lys Leu  Lys Asp Trp Glu Gly  Gly Leu Asp
                995                 1000                1005

Glu Gln  Arg Leu Ser Ala Asp  Ser Gly Tyr Ile Ile  Pro Leu Pro
    1010                1015                1020

Asp Ile  Asp Pro Val Pro Glu  Glu Glu Asp Leu Gly  Lys Arg Asn
    1025                1030                1035

Arg His  Ser Ser Gln Thr Ser  Glu Glu Ser Ala Ile  Glu Thr Gly
    1040                1045                1050

Ser Ser Ser Ser Thr Phe Ile  Lys Arg Glu Asp Glu  Thr Ile Glu
    1055                1060                1065

Asp Ile  Asp Met Met Asp Asp  Ile Gly Ile Asp Ser  Ser Asp Leu
    1070                1075                1080

Val Glu  Asp Ser Phe Leu
    1085

<210> SEQ ID NO 2
<211> LENGTH: 211
<212> TYPE: PRT
<213> ORGANISM: Homo sapiens
```

```
<400> SEQUENCE: 2

Met Arg Thr Leu Ala Cys Leu Leu Leu Gly Cys Gly Tyr Leu Ala
1               5                   10                  15

His Val Leu Ala Glu Glu Ala Glu Ile Pro Arg Glu Val Ile Glu Arg
            20                  25                  30

Leu Ala Arg Ser Gln Ile His Ser Ile Arg Asp Leu Gln Arg Leu Leu
            35                  40                  45

Glu Ile Asp Ser Val Gly Ser Glu Asp Ser Leu Asp Thr Ser Leu Arg
50                  55                  60

Ala His Gly Val His Ala Thr Lys His Val Pro Glu Lys Arg Pro Leu
65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
            115                 120                 125

Cys Thr Gly Cys Cys Asn Thr Ser Ser Val Lys Cys Gln Pro Ser Arg
130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Gly Arg Pro Arg Glu Ser Gly Lys Lys Arg Lys Arg Lys Arg Leu
            195                 200                 205

Lys Pro Thr
        210

<210> SEQ ID NO 3
<211> LENGTH: 104
<212> TYPE: PRT
<213> ORGANISM: Homo sapiens

<400> SEQUENCE: 3

Gly Leu Val Lys Pro Leu Glu Thr Leu Ser Leu Thr Cys Ser Val Ser
1               5                   10                  15

Gly Gly Ser Val Ser Asp Gly Ser Tyr Phe Trp Asn Trp Ile Arg Gln
            20                  25                  30

Pro Pro Gly Lys Gly Leu Glu Trp Ile Gly Tyr Ala Tyr Ser Arg Gly
            35                  40                  45

Thr Thr Asn Tyr Ser Pro Ser Leu Lys Gly Arg Ile Thr Ile Ser Val
50                  55                  60

Asp Lys Ser Lys Asn Gln Ile Ser Leu Lys Leu Thr Ser Val Thr Pro
65                  70                  75                  80

Ala Asp Thr Ala Val Tyr Tyr Cys Ala Arg Asp Ser Phe Glu Ile Trp
                85                  90                  95

Gly Gln Gly Thr Met Val Thr Val
            100

<210> SEQ ID NO 4
<211> LENGTH: 107
<212> TYPE: PRT
<213> ORGANISM: Homo sapiens
```

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Leu Gln Ser Gly Val Pro Ser Lys Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Tyr
                85                  90                  95

Thr Phe Gly Gln Gly Thr Lys Leu Glu Ile Lys
            100                 105

<210> SEQ ID NO 5
<211> LENGTH: 112
<212> TYPE: PRT
<213> ORGANISM: Homo sapiens

<400> SEQUENCE: 5

Gln Ser Val Leu Thr Gln Pro Pro Ser Ala Ser Gly Thr Pro Gly Gln
1               5                   10                  15

Ser Ile Thr Ile Ser Cys Ser Gly Ser Asp Ser Asn Ile Gly Thr Asn
            20                  25                  30

Tyr Val Tyr Trp Tyr Gln Gln Leu Ser Gly Met Ala Pro Lys Leu Leu
        35                  40                  45

Ile Tyr Arg Asn His Gln Arg Pro Ala Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Glu Asp Gly Leu
                85                  90                  95

Ser Gly Pro Leu Trp Val Phe Gly Gly Thr Lys Leu Thr Val Leu
            100                 105                 110

<210> SEQ ID NO 6
<211> LENGTH: 113
<212> TYPE: PRT
<213> ORGANISM: Homo sapiens

<400> SEQUENCE: 6

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asp Asn Lys Asn Tyr Leu Ala Trp Tyr Gln Gln Lys Pro Gly Gln
        35                  40                  45

Pro Pro Lys Leu Leu Leu Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Lys Thr Phe Gly Gln Gly Thr Lys Val Glu Ile
                100                 105                 110
Lys

<210> SEQ ID NO 7
<211> LENGTH: 110
<212> TYPE: PRT
<213> ORGANISM: Homo sapiens

<400> SEQUENCE: 7

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln His Pro Gly Lys Ala Pro Lys Leu
            35                  40                  45

Met Ile Tyr Glu Val Ser His Arg Pro Ser Gly Val Ser Asn Arg Phe
        50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Ser Ser Tyr Thr Ser Ser
                85                  90                  95

Ser His Val Val Phe Gly Gly Gly Thr Lys Leu Thr Val Leu
                100                 105                 110

<210> SEQ ID NO 8
<211> LENGTH: 122
<212> TYPE: PRT
<213> ORGANISM: Homo sapiens

<400> SEQUENCE: 8

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Tyr Ile Ser Ser Ser Ser Ser Thr Ile Tyr Tyr Ala Asp Ser Val
        50                  55                  60

Lys Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Val Tyr Tyr Cys
                85                  90                  95

Ala Arg Val Gly Tyr Asp Phe Trp Ser Asp Tyr Tyr Pro Tyr Tyr Tyr
                100                 105                 110

Tyr Tyr Met Asp Val Trp Gly Lys Gly Thr
            115                 120

<210> SEQ ID NO 9
<211> LENGTH: 121
<212> TYPE: PRT
<213> ORGANISM: Homo sapiens

<400> SEQUENCE: 9

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
                20                  25                  30

```
Ser Tyr Tyr Trp Ser Trp Ile Arg Gln Pro Ala Gly Lys Gly Leu Glu
             35                  40                  45

Trp Ile Gly Arg Ile Tyr Thr Ser Gly Ser Thr Asn Tyr Asn Pro Ser
 50                      55                  60

Leu Lys Ser Arg Val Thr Ile Ser Val Asp Thr Ser Lys Asn Gln Phe
65                      70                  75                  80

Ser Leu Lys Leu Ser Ser Val Thr Ala Ala Asp Thr Ala Val Tyr Tyr
                 85                  90                  95

Cys Ala Arg Asp Thr Pro Lys Thr Asn Leu Asn Trp Asn Tyr Val Glu
            100                 105                 110

Trp Phe Asp Pro Trp Gly Gln Gly Thr
            115                 120

<210> SEQ ID NO 10
<211> LENGTH: 102
<212> TYPE: PRT
<213> ORGANISM: Homo sapiens

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
             20                  25                  30

Leu Ala Trp Phe Gln Gln Lys Pro Gly Lys Ala Pro Lys Ser Leu Ile
         35                  40                  45

Tyr Ala Ala Ser Ser Leu Gln Ser Gly Val Pro Ser Lys Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Tyr
                85                  90                  95

Thr Phe Gly Gln Gly Thr
            100

<210> SEQ ID NO 11
<211> LENGTH: 105
<212> TYPE: PRT
<213> ORGANISM: Homo sapiens

<400> SEQUENCE: 11

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Val Gly Ala Gly
             20                  25                  30

Tyr Asp Val His Trp Tyr Gln Gln Leu Pro Gly Thr Ala Pro Lys Leu
         35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ala Leu Val Phe Gly Gly Gly Thr
            100                 105
```

```
<210> SEQ ID NO 12
<211> LENGTH: 245
<212> TYPE: PRT
<213> ORGANISM: Homo sapiens

<400> SEQUENCE: 12
```

Gln Val Gln Leu Gln Glu Ser Gly Pro Gly Leu Val Lys Pro Leu Glu
1               5                   10                  15

Thr Leu Ser Leu Thr Cys Ser Val Ser Gly Ser Val Ser Asp Gly
            20                  25                  30

Ser Tyr Phe Trp Asn Trp Ile Arg Gln Pro Pro Gly Lys Gly Leu Glu
        35                  40                  45

Trp Ile Gly Tyr Ala Tyr Ser Arg Gly Thr Thr Asn Tyr Ser Pro Ser
    50                  55                  60

Leu Lys Gly Arg Ile Thr Ile Ser Val Asp Lys Ser Lys Asn Gln Ile
65                  70                  75                  80

Ser Leu Lys Leu Thr Ser Val Thr Pro Ala Asp Thr Ala Val Tyr Tyr
                85                  90                  95

Cys Ala Arg Asp Ser Phe Glu Ile Trp Gly Gln Gly Thr Met Val Thr
            100                 105                 110

Val Ala Ser Ala Ser Thr Lys Gly Pro Ser Val Asp Ile Gln Met Thr
        115                 120                 125

Gln Ser Pro Asp Ser Leu Ala Val Ser Leu Gly Glu Arg Ala Thr Ile
    130                 135                 140

Asn Cys Lys Ser Ser Gln Ser Val Leu Tyr Ser Ser Asp Asn Lys Asn
145                 150                 155                 160

Tyr Leu Ala Trp Tyr Gln Gln Lys Pro Gly Gln Pro Pro Lys Leu Leu
                165                 170                 175

Leu Tyr Trp Ala Ser Thr Arg Glu Ser Gly Val Pro Asp Arg Phe Ser
            180                 185                 190

Gly Ser Gly Ser Gly Thr Asp Phe Thr Leu Thr Ile Ser Ser Leu Gln
        195                 200                 205

Ala Glu Asp Val Ala Val Tyr Tyr Cys Gln Gln Tyr Tyr Ser Thr Pro
    210                 215                 220

Lys Thr Phe Gly Gln Gly Thr Lys Val Glu Ile Lys Arg Thr Val Ala
225                 230                 235                 240

Ala Pro Ser Val Phe
                245

```
<210> SEQ ID NO 13
<211> LENGTH: 20
<212> TYPE: DNA
<213> ORGANISM: Artificial Sequence
<220> FEATURE:
<223> OTHER INFORMATION: synthetic primer

<400> SEQUENCE: 13
agggccaaga cgaagacatc                                               20

<210> SEQ ID NO 14
<211> LENGTH: 21
<212> TYPE: DNA
<213> ORGANISM: Artificial Sequence
<220> FEATURE:
<223> OTHER INFORMATION: synthetic primer

<400> SEQUENCE: 14
agatcacgtc atcgcacaac a                                             21
```

<210> SEQ ID NO 15
<211> LENGTH: 22
<212> TYPE: DNA
<213> ORGANISM: Artificial Sequence
<220> FEATURE:
<223> OTHER INFORMATION: synthetic primer

<400> SEQUENCE: 15
aggtcaaaca ggagcccgtg gg                                          22

<210> SEQ ID NO 16
<211> LENGTH: 21
<212> TYPE: DNA
<213> ORGANISM: Artificial Sequence
<220> FEATURE:
<223> OTHER INFORMATION: synthetic primer

<400> SEQUENCE: 16
gcacctggga agcctggagg g                                           21

<210> SEQ ID NO 17
<211> LENGTH: 20
<212> TYPE: DNA
<213> ORGANISM: Artificial Sequence
<220> FEATURE:
<223> OTHER INFORMATION: synthetic primer

<400> SEQUENCE: 17
taggccattg tgtatgcagc                                             20

<210> SEQ ID NO 18
<211> LENGTH: 21
<212> TYPE: DNA
<213> ORGANISM: Artificial Sequence
<220> FEATURE:
<223> OTHER INFORMATION: synthetic primer

<400> SEQUENCE: 18
acatgttcag ctttgtggac c                                           21

<210> SEQ ID NO 19
<211> LENGTH: 20
<212> TYPE: DNA
<213> ORGANISM: Artificial Sequence
<220> FEATURE:
<223> OTHER INFORMATION: synthetic primer

<400> SEQUENCE: 19
tgcaccacca actgcttagc                                             20

<210> SEQ ID NO 20
<211> LENGTH: 23
<212> TYPE: DNA
<213> ORGANISM: Artificial Sequence
<220> FEATURE:
<223> OTHER INFORMATION: synthetic primer

<400> SEQUENCE: 20
tgggatttcc attgatgaca agc                                         23

<210> SEQ ID NO 21
<211> LENGTH: 20
<212> TYPE: DNA
<213> ORGANISM: Artificial Sequence
<220> FEATURE:
<223> OTHER INFORMATION: synthetic primer

```
<400> SEQUENCE: 21
tccccatgaa cgaggaattc                                              20

<210> SEQ ID NO 22
<211> LENGTH: 21
<212> TYPE: DNA
<213> ORGANISM: Artificial Sequence
<220> FEATURE:
<223> OTHER INFORMATION: synthetic primer

<400> SEQUENCE: 22 gtgtacaaag␣ggcagggact t                                            21

<210> SEQ ID NO 23
<211> LENGTH: 21
<212> TYPE: DNA
<213> ORGANISM: Artificial Sequence
<220> FEATURE:
<223> OTHER INFORMATION: synthetic primer

<400> SEQUENCE: 23
agtccctgcc ctttgtacac a                                            21

<210> SEQ ID NO 24
<211> LENGTH: 19
<212> TYPE: DNA
<213> ORGANISM: Artificial Sequence
<220> FEATURE:
<223> OTHER INFORMATION: synthetic primer

<400> SEQUENCE: 24
cgatccgagg gcctcacta                                               19

<210> SEQ ID NO 25
<211> LENGTH: 21
<212> TYPE: DNA
<213> ORGANISM: Artificial Sequence
<220> FEATURE:
<223> OTHER INFORMATION: synthetic primer

<400> SEQUENCE: 25
cagtgctcag agctcgaaag t                                            21

<210> SEQ ID NO 26
<211> LENGTH: 20
<212> TYPE: DNA
<213> ORGANISM: Artificial Sequence
<220> FEATURE:
<223> OTHER INFORMATION: synthetic primer

<400> SEQUENCE: 26
gtgttcttcg acatcacggc                                              20

<210> SEQ ID NO 27
<211> LENGTH: 20
<212> TYPE: DNA
<213> ORGANISM: Artificial Sequence
<220> FEATURE:
<223> OTHER INFORMATION: synthetic primer

<400> SEQUENCE: 27
caggtgcagc tgcaggagtc                                              20
```

```
<210> SEQ ID NO 28
<211> LENGTH: 23
<212> TYPE: DNA
<213> ORGANISM: Artificial Sequence
<220> FEATURE:
<223> OTHER INFORMATION: synthetic primer

<400> SEQUENCE: 28
gacatccaga tgacccagtc tcc                                            23

<210> SEQ ID NO 29
<211> LENGTH: 18
<212> TYPE: DNA
<213> ORGANISM: Artificial Sequence
<220> FEATURE:
<223> OTHER INFORMATION: synthetic primer

<400> SEQUENCE: 29
ggaaccacca actacagc                                                  18

<210> SEQ ID NO 30
<211> LENGTH: 21
<212> TYPE: DNA
<213> ORGANISM: Artificial Sequence
<220> FEATURE:
<223> OTHER INFORMATION: synthetic primer

<400> SEQUENCE: 30
gccccagatt tcaaaagaat c                                              21

<210> SEQ ID NO 31
<211> LENGTH: 20
<212> TYPE: DNA
<213> ORGANISM: Artificial Sequence
<220> FEATURE:
<223> OTHER INFORMATION: synthetic primer

<400> SEQUENCE: 31
tcctttactg ggcatctacc                                                20

<210> SEQ ID NO 32
<211> LENGTH: 18
<212> TYPE: DNA
<213> ORGANISM: Artificial Sequence
<220> FEATURE:
<223> OTHER INFORMATION: synthetic primer

<400> SEQUENCE: 32
cccttggccg aacgtctt                                                  18

<210> SEQ ID NO 33
<211> LENGTH: 18
<212> TYPE: DNA
<213> ORGANISM: Artificial Sequence
<220> FEATURE:
<223> OTHER INFORMATION: synthetic primer

<400> SEQUENCE: 33
tcggtcactc tgttcccg                                                  18

<210> SEQ ID NO 34
<211> LENGTH: 18
<212> TYPE: DNA
<213> ORGANISM: Artificial Sequence
<220> FEATURE:
<223> OTHER INFORMATION: synthetic primer
```

```
<400> SEQUENCE: 34
atctgccttc caggccac                                                 18

<210> SEQ ID NO 35
<211> LENGTH: 20
<212> TYPE: DNA
<213> ORGANISM: Artificial Sequence
<220> FEATURE:
<223> OTHER INFORMATION: synthetic primer

<400> SEQUENCE: 35
tggctgcacc atctgtcttc                                               20

<210> SEQ ID NO 36
<211> LENGTH: 20
<212> TYPE: DNA
<213> ORGANISM: Artificial Sequence
<220> FEATURE:
<223> OTHER INFORMATION: synthetic primer

<400> SEQUENCE: 36
ctatcccaga gaggccaaag                                               20
```